United States Patent
Bonafoux et al.

(10) Patent No.: US 8,101,645 B2
(45) Date of Patent: Jan. 24, 2012

(54) THIENOPYRROLES AND PYRROLOTHIAZOLES AS NEW THERAPEUTIC AGENTS

(75) Inventors: Dominique F. Bonafoux, Cambridge, MA (US); Xiaoyun Wu, Westborough, MA (US)

(73) Assignee: Abbott Laboratories, Abbott Park, IL (US)

( * ) Notice: Subject to any disclaimer, the term of this patent is extended or adjusted under 35 U.S.C. 154(b) by 115 days.

(21) Appl. No.: 12/378,308

(22) Filed: Feb. 13, 2009

(65) Prior Publication Data

US 2009/0209609 A1 Aug. 20, 2009

Related U.S. Application Data

(60) Provisional application No. 61/066,046, filed on Feb. 15, 2008.

(51) Int. Cl.
*A61K 31/407* (2006.01)
*C07D 495/04* (2006.01)

(52) U.S. Cl. ........................ 514/412; 548/453

(58) Field of Classification Search ................ 514/412; 548/453
See application file for complete search history.

(56) References Cited

U.S. PATENT DOCUMENTS 7,517,875 B2 * 4/2009 Matsumoto et al. ....... 514/223.2

FOREIGN PATENT DOCUMENTS

| WO | 2005/102338 A1 | 11/2005 |
| WO | 2005/123731 A2 | 12/2005 |

OTHER PUBLICATIONS

S.R. Vippagunta, et al. Advanced. Drug Delivery Rev. (2001) 48, pp. 1-26.*
Frimurer, Thomas M., et al., "A physicogenetic method to assign ligand-binding relationships between 7TM receptors", Bioorganic & Medicinal Chemistry Letters, 2005, vol. 15(16,15): 3707-3712 .
Olsen, Richard K., et al., "The Synthesis of N-Benzylthieno [2,3-b] pyrrole", J. Org. Chem., 1965, vol. 30: 184-187.
Wensbo, David, et al., "Indole-3-Actetic Acids and Hetero Analogues by One Pot Synthesis including Heck Cyclisation", Tetrahedron, 1995, vol. 51(37):10323-10342.
Binder, Dieter, et al., "Thiophen als Strukturelement physiologisch aktiver Substanzen, 1. Mitt. Die Synthese von Derivaten der 4-Thieno [2,3-b]pyrrol-essigsaure.",Arch. Pharm. (Weinheim) 312, 169-174 (1979).

* cited by examiner

*Primary Examiner* — Sabiha Qazi
(74) *Attorney, Agent, or Firm* — Kenneth P. Zwicker; Gayle B. O'Brien

(57) ABSTRACT

The present invention is directed to novel compounds of Formula (I)

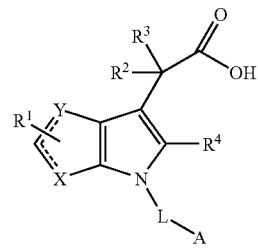

Formula I wherein the variables are defined as herein. The compounds of Formula (I) are useful as CRTH2 antagonists and as such would be useful in treating certain conditions and diseases, especially asthma, allergic asthma, allergic inflammation, rhinitis, allergic rhinitis or atopic dermatitis.

20 Claims, No Drawings

THIENOPYRROLES AND PYRROLOTHIAZOLES AS NEW THERAPEUTIC AGENTS

RELATED APPLICATION

This application claims priority to and the benefit of U.S. Provisional Application No. 61/066,046, filed Feb. 15, 2008.

BACKGROUND OF THE INVENTION

Mast cells are known to play an important role in allergic and immune responses through the release of a number of mediators, such as histamine, leukotrienes, cytokines, prostaglandin D2, etc.

Prostaglandin D2 (PGD2) is the major metabolite produced by the action of cyclooxygenase on arachadonic acid by mast cells in response to allergen challenge (R. A. Lewis et al; *J. Immunol.*, 1982, 129 (4), 1627) and is also produced by macrophages and Th2 lymphocytes.

PGD2 has been detected in high concentrations in patients with systemic mastocytosis (J. L. II Roberts et al; *Trans. Ass. Am. Phys.*, 1980, 93, 141), allergic rhinitis (R. M. Naclerio et al; *Am. Rev. Respir. Dis.*, 1983, 128 (4), 597; M. S. Brown et al; *Arch. Otolarynol. Head Neck Surg.*, 1987, 113 (2), 179; B. Lebel et al; *J. Allergy Clin. Immunol.*, 1988, 82, 869) and bronchial asthma (J. J. Murray et al; *N. Engl. J. Med.*, 1986, 315 (13), 800).

PGD2-driven exaggerated allergic inflammation and inflammatory responses have been demonstrated in mice and rats. Transgenic mice over expressing PGD2 synthase exhibit an enhanced pulmonary eosinophilia and increased levels of Th2 cytokines in response to allergen challenge (Y. Fujitani et al; *J. Immunol.*, 2002, 168 (1), 443). Also, exogenously administered CRTH2 agonist 13,14-dihydro-15-keto-PGD$_2$ (DK-PGD$_2$) enhances the allergic response in sensitized mice (I. Spik et al; *J. Immunol*, 2005, 174 (6), 3703). In rats intratracheal administration of CRTH2 agonists causes pulmonary eosinophilia whereas a DP agonist (BW 245C) or a TP agonist (1-BOP) have no effect (Y. Shirashi et al; *J. Pharmacol. Exp. Ther.*, 2005, 312, 954).

PGD2 mediates its effects through two high affinity 7-transmembrane receptors, the PGD2 receptor (DP) (Y. Boie et al; *J. Biol. Chem.*, 1995, 270, 18910) and the chemoattractant receptor-homologous molecule expressed on Th2 cells (CRTH2) (K. Nagata et al; *J. Immunol*, 1999, 162, 1278).

It has been shown that CRTH2 is expressed on cell types associated with allergic inflammation, such as Th2 cells, basophils and eosinophils and that its activation by PGD2 triggers the migration of these cell types (H. Hirai et at; *J. Exp. Med.*, 2001, 193, 255). CRTH2 was also reported to play a major role in neutrophil and eosinophil recruitment in a model of contact dermatitis (K. Takeshita et al; Int. Immunol., 2004, 16, 947-959).

Allergic asthma and allergic rhinitis are diseases that currently affect about 10% of the population, and this number appears to be increasing (R. K. Bush, Handbook of asthma and rhinitis. 1st ed. (1997), Abingdon: Blackwell Science, 270). Numerous classes of pharmaceutical agents are widely used to treat these diseases, for example, antihistamines, decongestants, β2 agonists, anticholinergics, methylxanthines, cromolyns, corticosteroids, and leukotriene modulators. Generally, the usefulness of these agents is limited by side effects and low efficacy. Accordingly, there is a critical medical need to identify pharmaceutically active compounds that interfere with key steps of the inflammatory and immunological processes that contribute to these disease states, and other inflammatory conditions.

The observations summarized above suggest that CRTH2 antagonists (P. Norman, *Exp. Opin. Ther. Patent*, 2005, 15(12), 1817) may have valuable properties for the treatment of diseases mediated by PGD2.

SUMMARY OF THE INVENTION

In a first embodiment, the invention provides compounds of Formula I

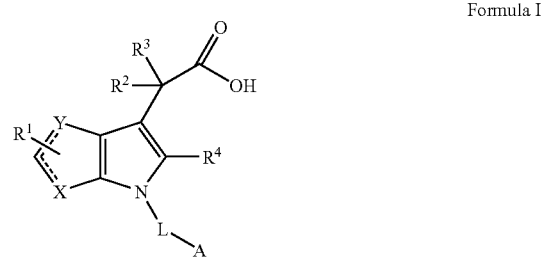

Formula I pharmaceutically acceptable salts, biologically active metabolites, solvates, hydrates, pro-drugs, enantiomers or stereoisomers thereof, wherein X is CH, S or N;
Y is CH, S or N;
L is CO, SO, S(O)$_2$ or (C$_1$-C$_4$)alkyl;
A is optionally substituted aryl, optionally substituted (C$_3$-C$_6$)cycloalkyl, optionally substituted heteroaryl, optionally substituted heterocyclyl or optionally substituted -aryl-S(O)$_2$—Z;
wherein Z is N(R$^5$)$_2$, optionally substituted (C$_1$-C$_6$)alkyl, optionally substituted (C$_3$-C$_6$)cycloalkyl or optionally substituted heterocyclyl;
R$^1$, R$^2$, R$^3$ and R$^4$ are independently H or (C$_1$-C$_4$)alkyl; and
R$^5$ is independently H, (C$_1$-C$_3$)alkyl, (C$_3$-C$_6$)cycloalkyl, —CO—(C$_1$-C$_6$)alkyl, or —CON(R$^1$)$_2$; provided that X and Y are not both S, not both CH$_2$ and not both N at the same time.

In a second embodiment, the invention provides compounds according to the first embodiment wherein X is CH.

In a third embodiment, the invention provides compounds according to any of the foregoing embodiments wherein Y is S.

In a fourth embodiment, the invention provides compounds according to any of the foregoing embodiments wherein L is S(O)$_2$.

In a fifth embodiment, the invention provides compounds according to any of the foregoing embodiments wherein A is optionally substituted phenyl, optionally substituted naphthyl, optionally substituted (C$_3$-C$_6$)cycloalkyl or optionally substituted dihydrobenzofuranyl; and R$^1$, R$^2$, R$^3$ and R$^4$ are independently H.

In a sixth embodiment, the invention provides compounds according to any of the foregoing embodiments wherein A is optionally substituted phenyl, optionally substituted dihydrobenzofuranyl or optionally substituted cyclopropyl;

wherein the phenyl, the dihydrobenzofuranyl or the cyclopropyl is optionally substituted with one or more substituents independently selected from halogen, CN, OH, —SO$_2$—(C$_1$-C$_6$)alkyl, —SO$_2$—(C$_3$-C$_6$)cycloalkyl, —O—(C$_1$-C$_4$)alkyl and optionally substituted (C$_1$-C$_6$)alkyl.

In a seventh embodiment, the invention provides compounds according to the first embodiment wherein X is S.

In an eighth embodiment, the invention provides compounds according to the first and seventh embodiments wherein Y is CH.

In a ninth embodiment, the invention provides compounds according to the first, seventh and eighth embodiments wherein L is $S(O)_2$ or $(C_1-C_4)$alkyl.

In a tenth embodiment, the invention provides compounds according to the first and seventh through ninth embodiments wherein A is optionally substituted aryl, optionally substituted heteroaryl or optionally substituted -aryl-$S(O)_2$—Z;

wherein Z is $N(R^5)_2$, optionally substituted $(C_1-C_6)$alkyl, optionally substituted $(C_3-C_6)$cycloalkyl or optionally substituted heterocyclyl; and $R^5$ is independently H, $(C_1-C_3)$alkyl, or $(C_3-C_6)$cycloalkyl, —CO—$(C_1-C_6)$alkyl, or —$CON(R^1)_2$.

In an eleventh embodiment, the invention provides compounds according to the first and seventh through tenth embodiments wherein $R^2$ and $R^3$ are H.

In a twelfth embodiment, the invention provides compounds compounds according to the first and seventh through eleventh embodiments wherein A is optionally substituted isoxazolyl, optionally substituted naphthyl, optionally substituted phenyl, optionally substituted pyridinyl or -optionally substituted phenyl-$S(O)_2$—Z;

wherein Z is $CH_3$, —$N(CH_3)_2$, —$N(CH_3)$cyclohexyl, optionally substituted morpholinyl or optionally substituted pyrrolidinyl.

In a thirteenth embodiment, the invention provides compounds according to the first and seventh through twelfth embodiments wherein A is optionally substituted by one or more substituents independently selected from halogen, CN, $CH_3$, —NH—C(O)—$CH_3$, $NHCON(CH_3)_2$, $CF_3$, —$S(O)_2CH_3$, optionally substituted $(C_1-C_4)$alkyl, —O—$(C_1-C_4)$alkyl and pyrazolyl.

In a fourteenth embodiment, the invention provides compounds according to the first and seventh through thirteenth embodiments wherein $R^1$ is $CH_3$ and $R^4$ is $CH_3$.

In a fifteenth embodiment, the invention provides compounds according to the first and seventh through fourteenth embodiments wherein $R^1$ is H and $R^4$ is H or $CH_3$.

In a sixteenth embodiment, the invention provides compounds according to the first and seventh through fifteenth embodiments wherein L is $CH_2$.

In a seventeenth embodiment, the invention provides compounds according to the first and seventh through sixteenth embodiments wherein A is optionally substituted isoxazolyl, optionally substituted phenyl or optionally substituted -phenyl-$S(O)_2$—Z;

wherein Z is $CH_3$, —$N(CH_3)_2$, —$N(CH_3)$cyclohexyl or optionally substituted morpholinyl.

In an eighteenth embodiment, the invention provides compounds according to the first and seventh through seventeenth embodiments wherein L is $S(O)_2$.

In a nineteenth embodiment, the invention provides compounds according to the first and seventh through eighteenth embodiments wherein A is optionally substituted naphthyl, optionally substituted phenyl, optionally substituted pyridinyl or optionally substituted -phenyl-$S(O)_2$—Z;

wherein Z is $CH_3$, —$N(CH_3)_2$, optionally substituted morpholinyl or optionally substituted pyrrolidinyl.

In a twentieth embodiment the invention provides a method of treating a condition in a patient comprising administering a therapeutically effective amount of a compound of any of the foregoing embodiments or a physiologically acceptable salt, pro-drug or biologically active metabolites thereof to said patient in need thereof, wherein the condition is asthma, allergic asthma, allergic inflammation, rhinitis, allergic rhinitis or atopic dermatitis.

In a twenty-first embodiment, the compounds of the invention are useful for the manufacture of medicaments.

DETAILED DESCRIPTION OF THE INVENTION

The present invention provides compounds of formula (I) or pharmaceutically acceptable salts thereof that have activity as pharmaceuticals in the treatment of diseases associated with elevated $PGD_2$ levels.

Compounds of formula (I) or pharmaceutically acceptable salts thereof are particularly useful as modulators of CRTH2 receptor activity, and may be used in the treatment (therapeutic or prophylactic) of conditions/diseases which are exacerbated or caused by excessive or unregulated production of PGD2 and its metabolites.

A compound of formula (I), a salt, pro-drug, or pharmaceutical compositions containing a therapeutically effective amount thereof can be useful in reducing tissue damage, airway inflammation, bronchial hyperreactivity, remodeling or disease progression when used for the treatment of inflammatory or obstructive airway diseases.

Inflammatory or obstructive airway diseases that can be treated with the compounds of the invention include asthma, both intrinsic (non-allergic) asthma and extrinsic (allergic) asthma, mild asthma, moderate asthma, severe asthma, bronchitis asthma, exercise induced asthma, occupational asthma, aspirin induced asthma, NSAIDs induced asthma and asthma induced following bacterial infection. In addition, compounds of the invention can also be useful to treat wheezing symptoms associated with airway diseases.

The compounds of the invention are also applicable to the treatment of other inflammatory or obstructive diseases, such as, but not limited to, acute lung injury (ALI), adult respiratory distress syndrome (ARDS), chronic obstructive pulmonary airways or lung disease (COPD, COAD or COLD), including chronic bronchitis or dyspnea associated therewith, emphysema, as well as exacerbation of airway hyperreactivity consequent to other drug therapy, in particular, other inhaled drug therapy, bronchitis (acute, arachidic, catarrhal, croupus, chronic or phthinoid bronchitis, pneumoconiosis (e.g., aluminosis, anthracosis, asbestosis, chalicosis, ptilosis, siderosis, silicosis, tabacosis and byssinosis)).

Eosinophilia and eosinophils-related disorders can also be treated with the compounds of the invention. Such disorders, include, but are not limited to, eosinophilic infiltration of pulmonary tissues, hypereosinophilia, eosinophilic pneumonia, parasitic infestation including tropical eosinophilia, bronchopulmonary aspergillosis, polyarteritis nodosa including Churg-Strauss syndrome, eosinophilic granuloma and eosinophil-related disorders affecting the airways that can be caused by drug-reactions.

Allergic conditions such as those of the skin, e.g., psoriasis, contact dermatitis, alopecia areata, erythema multiforma, dermatitis herpetiformis, scleroderma, vitiligo, hypersensitivity angiitis, urticaria, bullous pemphigoid, lupus erythematosus, pemphisus, epidermolysis bullosa acquisita, and especially atopic dermatitis can also be treated with the compounds of the invention.

Other PGD2 mediated diseases that can be prevented or treated by the compounds of the invention include, but are not limited to, food allergies, autoimmune diseases such as hyper IgE syndrome and systemic lupus erythematus, acne, multiple sclerosis, allograpfht rejection, reperfusion injury, rheumatoid arthritis, psoriatic arthritis and osteoarthritis.

WO 05/102338 describes CRTH2 receptor antagonists for the treatment of neuropathic pain. Therefore, compounds of the invention can be of use for the treatment of neuropathic pain.

Compounds of formula (I) of the invention can be used alone or in combination with other therapeutic agents to treat such diseases, e.g., a therapeutic agents being selected by the skilled artisan for its intended purpose. The co-therapies using the compounds of this invention with other drug substances can be for example used to potentiate the therapeutic efficacy of these drugs, to reduce the dosage of these drugs and possibly their side effects The combinations, which are part of this invention, can be the compounds of the present invention and at least one additional agent selected from anti-inflammatory, bronchodilatory, antihistamine or anti-tussive drug substances. The agents set forth below are for illustrative purposes and not intended to be limiting.

Preferred anti-inflammatory drugs include, but are not limited to, steroids, in particular, glucocorticosteroids, budesonide, beclamethasone dipropionate, fluticasone propionate, ciclesonide or mometasone furoate.

Preferred bronchodilatory drugs include anticholinergic or antimuscarinic agents, in particular but not limited to, ipratropium bromide, oxitropium bromide and tiotropium salts.

Preferred antihistamine drug substances include, but are not limited to, cetirizine hydrochloride, clemastine fumarate, promethazine, loratidine, desloratidine, diphenhydramine and fexofenadine hydrochloride.

In addition, combinations of the coumpunds of the invention with other anti-inflammatory drugs such as chemokine receptors antagonist drugs, for example, CCR-1, CCR-2, CCR-4, CCR-5, CCR-6, CCR-7, CCR-8, CCR-9, CCR-10, CXCR1, CXCR2, CXCR3, CXCR4, CXCR5 ansd especially CCR-3 antagonists may also be useful.

In this invention, the following definitions are applicable:

A "therapeutically effective amount" is an amount of a compound of Formula I or a combination of two or more such compounds, which inhibits, totally or partially, the progression of the condition or alleviates, at least partially, one or more symptoms of the condition. A therapeutically effective amount can also be an amount which is prophylactically effective.

"Physiologically acceptable salts" refers to those salts wich retain the biological effectiveness and properties of the free carboxylic acids, and which are obtained by reaction with pharmaceutically acceptable bases. Suitable salts include alkali metal or alkaline earth metal salts including, sodium, potassium, magnesium, calcium or zinc salts. Other suitable salts are those obtained by reaction with ammonia or other pharmaceutically acceptable organic amines or heterocyclic bases, such as, but not limited to, diethylamine, ethanolamine, diethanolamine, triethanolamine, ethylenediamine, benethamine, benzathine, piperazine, tromethamine, 4(2-hydroxyethyl)morpholine, 1-(2-hydroxyethyl)pyrrolidine, N-methyl glucamine, arginine, lysine. These salts can be prepared by methods known to the skilled in the art.

Certain compounds of formula I and their salts may exist in more than one crystal form and the present invention includes each crystal form and mixtures thereof.

Certain compounds of formula I and their salts may also exist in the form of solvates, for example hydrates, and the present invention includes each solvate and mixtures thereof.

Certain compounds of formula I may contain one or more chiral centers, and exist in different optically active forms. When compounds of formula I contain one chiral center, the compounds exist in two enantiomeric forms and the present invention includes both enantiomers and mixtures of enantiomers, such as racemic mixtures.

When a compound of formula I contains more than one chiral center, it may exist in diastereoisomeric forms. The present invention includes each diastereoisomer of compounds of formula I and mixtures thereof.

Certain compounds of formula I may exist in different tautomeric forms or as different geometric isomers, and the present invention includes each tautomer and/or geometric isomer of compounds of formula I and mixtures thereof.

Certain compounds of formula I may exist in different stable conformational forms which may be separable. Torsional asymmetry due to restricted rotation about an asymmetric single bond, for example because of steric hindrance or ring strain, may permit separation of different conformers. The present invention includes each conformational isomer of compounds of formula I and mixtures thereof and in particular geometric isomers when $R^1$ and $R^2$ are not both H.

Certain compounds of formula I may exist in zwitterionic form and the present invention includes each zwitterionic form of compounds of formula I and mixtures thereof. As used herein the term "pro-drug" refers to an agent which is converted into the parent drug in vivo by some physiological chemical process (e.g., a pro-drug on being brought to the physiological pH is converted to the desired drug form). Pro-drugs are often useful, for example they may be easier to administer than the parent drug or offer better oral bioavailability than the parent drug. An example, without limitation, of a pro-drug would be a compound of the present invention wherein it is administered as an hydrolizable ester (the "pro-drug"). Such hydrolyzable esters include but are not limited to the carboxylic acids wherein the free hydrogen is replaced by $(C_1-C_4)$alkyl, $(C_2-C_{12})$alkanoyloxymethyl, $(C_4-C_9)$1-(alkanoyloxy)ethyl, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N-$(C_1-C_2)$alkylamino$(C_2-C_3)$alkyl (such as β-dimethylaminoethyl), carbamoyl-$(C_1-C_2)$alkyl, N,N-di$(C_1-C_2)$-alkylcarbamoyl-$(C_1-C_2)$alkyl and piperidino-, pyrrolidino- or morpholino$(C_2-C_3)$alkyl.

The term "heterocyclic" or "heterocyclyl", as used herein, include non-aromatic, ring systems, including, but not limited to, monocyclic, bicyclic and tricyclic rings, which can be completely saturated or which can contain one or more units of unsaturation (for the avoidance of doubt, the degree of unsaturation does not result in an aromatic ring system and have 3 to 12 atoms including at least one heteroatom, such as nitrogen, oxygen, or sulfur). For purposes of exemplification, which should not be construed as limiting the scope of this invention, the following are examples of heterocyclic rings: azepines, azetidinyl, morpholinyl, oxopiperidinyl, oxopyrrolidinesyl, piperazinyl, piperidinyl, pyrrolidinyl, quinicludinyl, thiomorpholinyl, tetrahydropyranyl and tetrahydrofuranyl.

The term "heteroaryl" as used herein, include aromatic ring systems, including, but not limited to, monocyclic, bicyclic and tricyclic rings, and have 3 to 12 atoms including at least one heteroatom, such as nitrogen, oxygen, or sulfur. For purposes of exemplification, which should not be construed as limiting the scope of this invention: azaindolyl, benzo(b) thienyl, benzimidazolyl, benzofuranyl, benzoxazolyl, benzothiazolyl, benzothiadiazolyl, benzoxadiazolyl, furanyl, imidazolyl, imidazopyridinyl, indolyl, indolinyl, indazoles, isoindolinyl, isoxazolyl, isothiazolyl, oxadiazolyl, oxazolyl, purinyl, pyranyl, pyrazinyl, pyrazolyl, pyridinyl, pyrimidinyl, pyrrolyl, pyrrolo[2,3-d]pyrimidinyl, pyrazolo[3,4-d]pyrimidinyl, quinolinyl, quinazolinyl, thiazolyl, thiophenyl, tetrahydroindolyl, tetrazolyl, thiadiazolyl, thienyl, thiomorpholinyl, triazolyl or tropanyl.

When the term "substituted heterocyclic" (or heterocyclyl) or "substituted heteroaryl" is used, what is meant is that the heterocyclic group is substituted with one or more substituents that can be made by one of ordinary skill in the art and results in a molecule that is a CRTH2 antagonist. For purposes of exemplification, which should not be construed as limiting the scope of this invention, preferred substituents for the heterocycle of this invention are each independently selected from the optionally substituted group consisting of alkenyl, alkoxy, alkoxyalkoxy, alkoxyalkyl, alkoxycarbonyl, alkoxycarbonylheterocycloalkoxy, alkyl, alkylcarbonyl, alkylester, alkyl-O—C(O)—, alkyl-heterocyclyl, alkyl-cycloalkyl, alkyl-nitrile, alkynyl, amido groups, amino, aminoalkyl, aminocarbonyl, carbonylalkoxy, carboxamido, $CF_3$, CN, —C(O)H, —C(O)—C($CH_3$)$_3$, —OH, —C(O)-cycloalkyl, —C(O)-heterocyclyl, cycloalkyl, dialkylaminoalkoxy, dialkylaminocarbonylalkoxy, dialkylaminocarbonyl, halogen, heterocyclyl, a heterocycloalkyl group, heterocyclyloxy, hydroxyalkyl, nitro, $OCF_3$, oxo, phenyl, —$SO_2CH_3$, —$SO_2CR_3$, tetrazolyl, thienylalkoxy, trifluoromethylcarbonylamino, trifluoromethylsulfonamido, heterocyclylalkoxy, heterocyclyl-S(O)$_p$, cycloalkyl-S(O)$_p$, alkyl-S—, heterocyclyl-S, heterocycloalkyl, cycloalkylalkyl, heterocycolthio, cycloalkylthio, —$Z^{105}$—C(O)N(R)$_2$, —$Z^{105}$—N(R)—C(O)—$Z^{200}$, —$Z^{105}$—N(R)—S(O)$_2$—$Z^{200}$, —$Z^{105}$—N(R)—C(O)—N(R)—$Z^{200}$, —$Z^{105}$—S(O)$_p$—N(R)—$Z^{200}$, —N(R)—C(O)R, —OR—C(O)-heterocyclyl-OR, $R_c$ and —$CH_2OR_c$;

wherein $R_3$ is $C_1$-$C_4$ alkyl, $C_3$-$C_6$ cycloalkyl or phenyl;
wherein p is 0, 1 or 2;
where $R_c$ for each occurrence is independently hydrogen, optionally substituted alkyl, optionally substituted aryl, —($C_1$-$C_6$)—$NR_dR_e$, -E-($CH_2$)$_t$—$NR_dR_e$, -E-($CH_2$)$_t$—O-alkyl, -E-($CH_2$)$_t$—S-alkyl, or -E-($CH_2$)$_t$—OH;
wherein t is an integer from about 1 to about 6;
$Z^{105}$ for each occurrence is independently a covalent bond, alkyl, alkenyl or alkynyl; and
$Z^{200}$ for each occurrence is independently selected from an optionally substituted group selected from the group consisting of alkyl, alkenyl, alkynyl, phenyl, alkyl-phenyl, alkenyl-phenyl or alkynyl-phenyl;
E is a direct bond, O, S, S(O), S(O)$_2$, or $NR_f$, wherein $R_f$ is H or alkyl and $R_d$ and $R_e$ are independently H, alkyl, alkanoyl or $SO_2$-alkyl; or $R_d$, $R_e$ and the nitrogen atom to which they are attached together to form a five- or six-membered heterocyclic ring.

As used herein, "aliphatic" or "an aliphatic group" or notations such as "($C_0$-$C_8$)" include straight chained or branched hydrocarbons which are completely saturated or which contain one or more units of unsaturation, and, thus, includes alkyl, alkenyl, alkynyl and hydrocarbons comprising a mixture of single, double and triple bonds. When the group is a $C_0$ it means that the moiety is not present or in other words, it is a bond. As used herein, "alkyl" means $C_1$-$C_8$ and includes straight chained or branched hydrocarbons, which are completely saturated. Preferred alkyls are methyl, ethyl, propyl, butyl, pentyl, hexyl and isomers thereof. As used herein, "alkenyl" and "alkynyl" means $C_2$-$C_8$ and includes straight chained or branched hydrocarbons which contain one or more units of unsaturation, one or more double bonds for alkenyl and one or more triple bonds for alkynyl.

As used herein, aromatic groups (or aryl groups) include aromatic carbocyclic ring systems (e.g. phenyl and cyclopentyldienyl) and fused polycyclic aromatic ring systems (e.g. naphthyl, biphenylenyl and 1,2,3,4-tetrahydronaphthyl).

As used herein, cycloalkyl means $C_3$-$C_{12}$ monocyclic or multicyclic (e.g., bicyclic, tricyclic, etc.) hydrocarbons that is completely saturated or has one or more unsaturated bonds but does not amount to an aromatic group. Preferred examples of a cycloalkyl group are cyclopropyl, cyclobutyl, cyclopentyl, cyclopentenyl, cyclohexyl and cyclohexenyl.

As used herein, many moieties or substituents are termed as being either "substituted" or "optionally substituted". When a moiety is modified by one of these terms, unless otherwise noted, it denotes that any portion of the moiety that is known to one skilled in the art as being available for substitution can be substituted, which includes one or more substituents, where if more than one substituent then each substituent is independently selected. Such means for substitution are well-known in the art and/or taught by the instant disclosure. For purposes of exemplification, which should not be construed as limiting the scope of this invention, some examples of groups that are substituents are: alkenyl groups, alkoxy group (which itself can be substituted, such as —O—$C_1$-$C_6$-alkyl-OR, —O—$C_1$-$C_6$-alkyl-N(R)$_2$, and $OCF_3$), alkoxyalkoxy, alkoxycarbonyl, alkoxycarbonylpiperidinyl-alkoxy, alkyl groups (which itself can also be substituted, such as —$C_1$-$C_6$-alkyl-OR, —$C_1$-$C_6$-alkyl-N(R)$_2$, and —$CF_3$), alkylamino, alkylcarbonyl, alkylester, alkylnitrile, alkylsulfonyl, amino, aminoalkoxy, $CF_3$, COH, COOH, CN, cycloalkyl, dialkylamino, dialkylaminoalkoxy, dialkylaminocarbonyl, dialkylaminocarbonylalkoxy, dialkylaminosulfonyl, where R is groups such as alkyl, heterocycloalkyl (which can be substituted), heterocyclyl, etc., which can be substituted), halogen or halo group (F, Cl, Br, I), hydroxy, morpholinoalkoxy, morpholinoalkyl, nitro, oxo, $OCF_3$, optionally substituted phenyl, —S(O)$_2$($C_1$-$C_4$)alkyl, —S(O)$_2CF_3$, —S(O)$_2$cycloalkyl, —S(O)$_2$NR'R" where R' and R" are independently H, alkyl or heterocyclyl, sulfonyl, N-alkylamino or N,N-dialkylamino (in which the alkyl groups can also be substituted).

One or more compounds of this invention can be administered to a human patient by themselves or in pharmaceutical compositions where they are mixed with biologically suitable carriers or excipient(s) at doses to treat or ameliorate a disease or condition as described herein. Mixtures of these compounds can also be administered to the patient as a simple mixture or in suitable formulated pharmaceutical compositions. A therapeutically effective dose refers to that amount of the compound or compounds sufficient to result in the prevention or attenuation of a disease or condition as described herein. Techniques for formulation and administration of the compounds of the instant application may be found in references well known to one of ordinary skill in the art, such as "Remington's Pharmaceutical Sciences," Mack Publishing Co., Easton, Pa., latest edition.

Suitable routes of administration for the compounds of the invention may, for example, include oral administration, e.g., in the form of tablets, capsules or drageas, inhalation, intranasal administration, topical administration, intravenous injection, eyedrops, rectal and transmucosal administration.

The teachings of all references, including journal articles, patents and published patent applications, are incorporated herein by reference in their entirety.

Enzyme Assays
Radioligand Binding Assay

Binding was performed on membranes prepared from HEK293.F cells (Invitrogen) transiently transfected with human CRTH2 cDNA. Assays were performed in a final volume of 100 µL of assay buffer (50 m HEPES pH 7.0, 10 mM $MnCl_2$, 1 mM EDTA, 0.2% BSA) in a 96-well round-bottom polypropylene plate (Costar 3357). Compounds were serially diluted in 100% DMSO then diluted into 10% DMSO/assay buffer before addition of 10 µl to the assay plate (Final DMSO conc. in assay is 1% (v/v)). 40 µL of CRTH2 membranes (20 ug/well) was added to each well and incubated at room temperature for 10 min. 50 µL of [$^3$H]-$PGD_2$ (PerkinElmer NET-616, 171 Ci/mmol) was added to each well (Final conc. 1 nM) and incubated at room temperature for 1 hour. Total and non-specific binding was determined in absence and presence of 10 µM unlabeled $PGD_2$. Assay plates were harvested (PerkinElmer Filtermate Harvester) onto a GF/C filter plate (pre-soaked in 0.3% (v/v) polyethyleneimine) and washed with 5 well volumes of cold wash buffer (50 mM HEPES pH 7.0, 500 mM NaCl). Plates were dried for 1 hour in a vacuum oven, 50 µL of Microscint-20 added to each well and bound radioactivity quantified by scintillation counting (PerkinElmer Topcount NXT HTS). $IC_{50}$s were determined by non-linear regression using the following four-parameter logistic equation:

$$Y = \text{Bottom} + (\text{Top} - \text{Bottom})/(1 + 10^{((\log IC_{50} - X)*\text{Hillslope})})$$

where Y denotes specific binding, X is logarithmic concentration of antagonist, top is total binding and bottom is non-specific binding.

Compounds of the invention may be prepared using the synthetic transformations illustrated in Schemes I-IV. Starting materials are commercially available or may be prepared by the procedures described herein, by literature procedures, or by procedures that would be well known to one skilled in the art of organic chemistry.

Methods for preparing thienopyrroles 4 and 5 of the invention are illustrated in Scheme I. Unsubstituted thienopyrrole ethyl ester 1 ($R^1=R^2=R^3=H$; $R^4=Et$) is prepared from the tert-butyl 3-iodothiophen-2-ylcarbamate as described by Wensbo D., Annby U. and Gronowitz S. in *Tetrahedron*, 1995, 51(37), 10323.

A suitably substituted thienopyrrole ester 1 may be reacted in a number of ways. For example, reaction with a sulfonyl chloride or a benzyl halide using General Procedures A and B respectively yield esters 2 and 3. Subsequent saponification of the ester group can be performed using conditions known in the literature (see Greene, T. W. and Wuts, P. G. M. "Protective Groups in Organic Synthesis, $3^{rd}$ Edition", 1999, Wiley-Interscience, or General Procedure C and D) to afford thienopyrroles 4 and 5.

Scheme I:

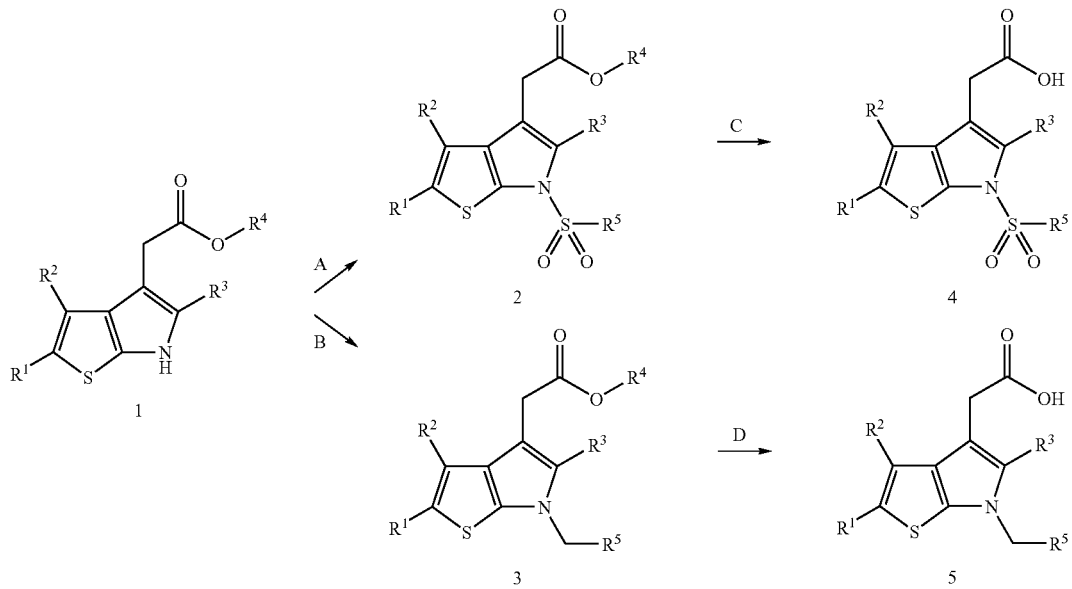

As shown in Scheme II, substituted thienopyrrole esters 1 are synthesized from the tert-butyl 3-halothiophen-2-ylcarbamates 9, via a "one-pot two step sequence" involving an alkylation with crotonate 12 followed by an intramolecular Heck coupling using conditions described in General Procedure H to give Boc-protected intermediate 13 that is deprotected using methods known in the literature (see Greene, T. W. and Wuts, P. G. M. "Protective Groups in Organic Synthesis, $3^{rd}$ Edition", 1999, Wiley-Interscience, or General Procedure I). The tert-butyl 3-halothiophen-2-ylcarbamates 9 can be prepared from commercially available thiophene-2-carboxylates 6 ($R^4=H$, $R^3=$alkyl) or 3-halothiophene-2-carboxylic acids 10 ($R^4=$halogen, $R^3=H$). For example, a thiophene-2-carboxylate 6 ($R^4=H$) can be saponified to the corresponding thiophene-2-carboxylic acid 7 ($R^4=H$) using conditions known in the literature (see Greene, T. W. and Wuts, P. G. M. "Protective Groups in Organic Synthesis, $3^{rd}$ Edition", 1999, Wiley-Interscience, or General Procedure E). Acid 7 ($R^4=H$) can be subjected to a Curtius rearrangement using methods known to one skilled in the art (see, for example, Y. Yang, A.-B. Hörnfeldt, S. Gronowitz, *Chemica*

Scripta, 1998, 28, 275 or General Procedure F). The resulting tert-butyl thiophen-2-ylcarbamates 8 ($R^4$=H) can be halogenated using methods known to one skilled in the art (see, for example, Larock, R. C. "Comprehensive Organic Transformations: A Guide to Functional Group Preparations, $2^{nd}$ edition", 1999, Wiley-VCH ) and in particular brominated, with bromine, to give the tert-butyl 3-bromothiophen-2-ylcarbamates 9 (Hal=Br) using General Procedures G.

Similarly, 3-halothiophene-2-carboxylates 10 ($R^4$=halogen, $R^3$=alkyl) can be converted to tert-butyl 3-halothiophen-2-ylcarbamates 9 with a sequence of saponification using General Procedures E to give 11 ($R^4$=halogen) and Curtius Rearrangement using General Procedure F.

Scheme II:

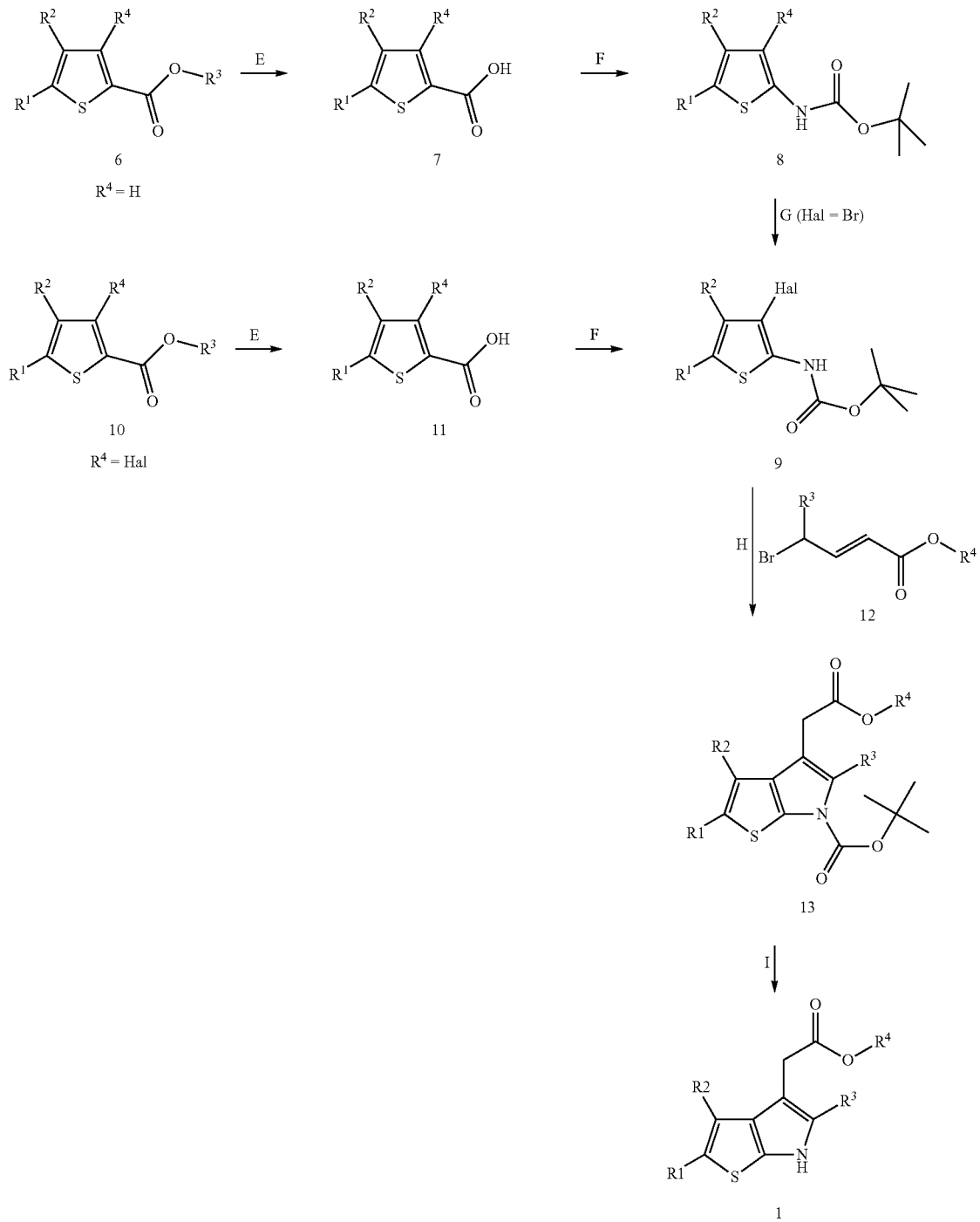

Scheme III:

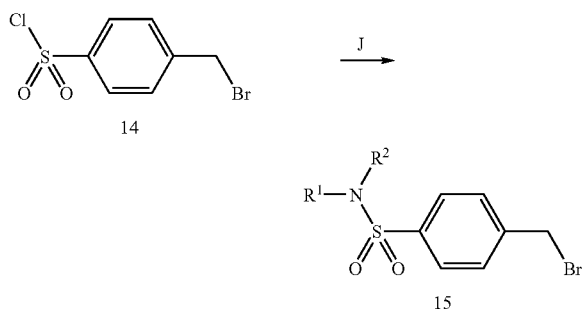

Non commercially available 4-(bromomethyl)benzene-sulfonamides to be used in General Procedure B of Scheme I can be prepared using methods known to one skilled in the art (see, for example, Larock, R. C. "Comprehensive Organic Transformations: A Guide to Functional Group Preparations, 2$^{nd}$ edition", 1999, Wiley-VCH).

For example, 4-(bromomethyl)benzenesulfonamides 15 can be synthesized by reacting the 4-(bromomethyl)benzene-1-sulfonyl chloride 14 and an amine using General Procedure J, as shown in Scheme III.

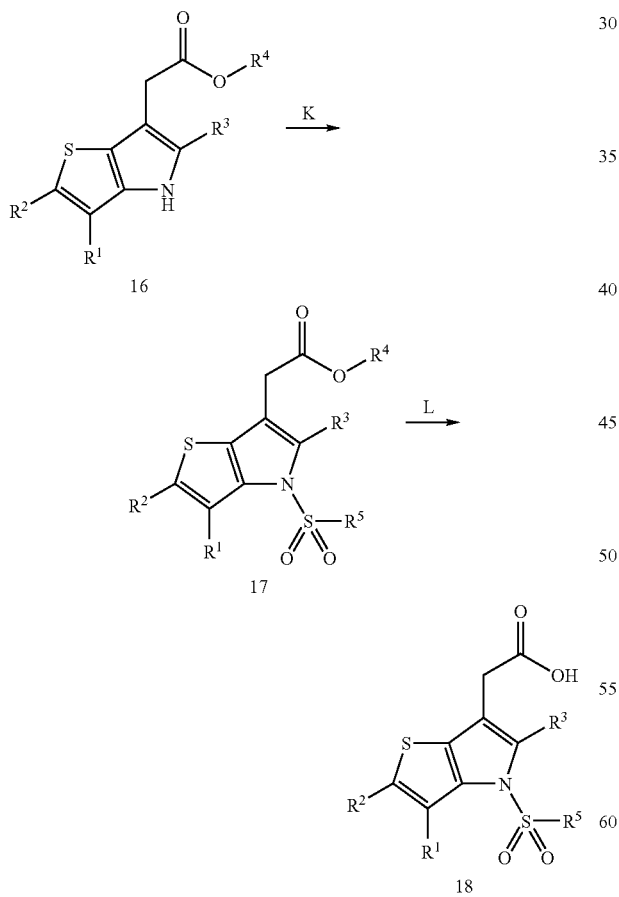

The preparation of thienopyrroles 18 of the invention is illustrated in Scheme IV. The unsubstituted thienopyrrole ethyl ester 16 ($R^1=R^2=R^3=H$; $R^4=Et$) is prepared from the tert-butyl 2-iodothiophen-3-ylcarbamate as described by Wensbo D., Annby U. and Gronowitz S. in tetrahedron, 1995, 51(37), 10323.

Substituted thienopyrrole esters 16 can be synthesized from tert-butyl 2-iodo- or tert-butyl 2-bromo-thiophen-3-yl-carbamates, using the same sequence as that described in Scheme I, via a "one-pot two step sequence" involving an alkylation with a crotonate 12 followed by an intramolecular Heck coupling using conditions described in General Procedure H and a Boc-deprotection using General Procedure I.

A suitably substituted ethyl 2-(5-methyl-4H-thieno[3,2-b]pyrrol-6-yl)acetate 16 can be further reacted in a number of ways.

For example, reaction with a sulfonyl chloride using General Procedure K yields ester 17. Saponification of the ester group in 17 can be performed using conditions known in the literature (see Greene, T. W. and Wuts, P. G. M. "Protective Groups in Organic Synthesis, 3$^{rd}$ Edition", 1999, Wiley-Interscience, or General Procedure L) to afford thienopyrroles 18.

Abbreviations
ACN Acetonitrile
Boc tert-Butoxycarbonyl
DCE Dichloroethane
DCM Dichloromethane (methylene chloride)
DIPEA N,N-Diisopropylethylamine
DMA N,N-Dimethylacetamide
DMAP 4-(Dimethylamino)pyridine
DME 1,2-Dimethoxyethane
DMF N,N-Dimethylformamide
DMSO Dimethyl sulfoxide
equiv Equivalent (molar equivalent)
EtOAc Ethyl acetate
EtOH Ethyl alcohol
Et$_2$O Diethyl ether
HOAc Acetic acid
HPLC High-pressure liquid chromatography
IPA Isopropyl alcohol
LC/MS Liquid chromatography/mass spectrometry
M Molar
MeOH Methyl alcohol
N Normal
NIS N-Iodosuccinimide
NMR Nuclear magnetic resonance
n-PrOH n-Propyl alcohol
PPh$_3$ Triphenylphosphine
RP-HPLC Reverse-phase high-pressure liquid chromatography
R$_f$ Retention factor
R$_t$ Retention time
TEA Triethylamine
TFA Trifluoroacetic acid
THF Tetrahydrofuran
TLC Thin layer chromatography
UV Ultraviolet light
wt % Weight percent

GENERAL PROCEDURES AND EXAMPLES

The general synthetic schemes that were utilized to construct the majority of compounds disclosed in this application are described below in Schemes 1-16. These schemes are provided for illustrative purposes only and are not to be construed as limiting the scope of the invention.

Scheme 1. Coupling of a 2-(6H-thieno[2,3-b]pyrrol-4-yl)acetate with sulfonylchlorides (General Procedure A)

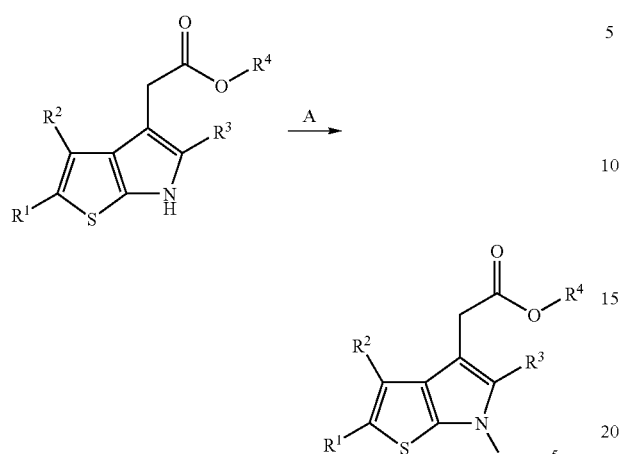

Scheme 2. Coupling of a 2-(6H-thieno[2,3-b]pyrrol-4-yl)acetate with benzylhalides (General Procedure B)

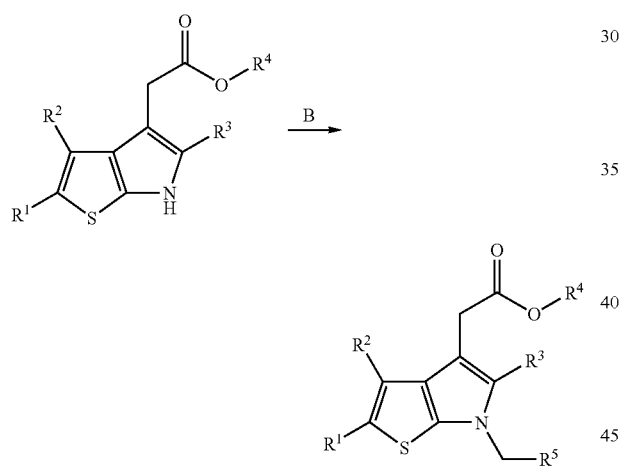

Scheme 3. Saponification of a 2-(6-(sulfonyl)-6H-thieno[2,3-b]pyrrol-4-yl)acetate (General Procedure C)

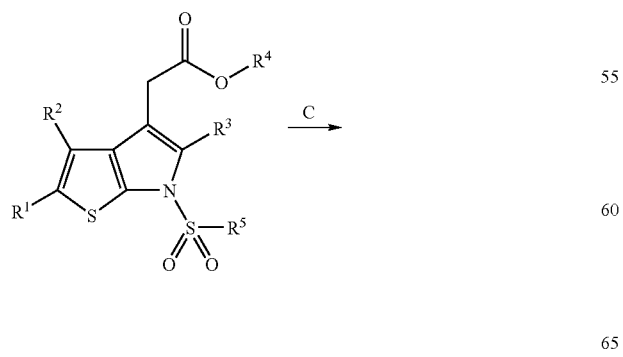

-continued

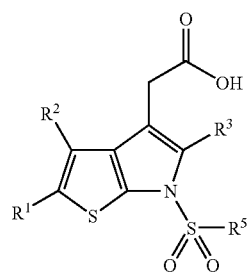

Scheme 4. Saponification of a 2-(6-benzyl-6H-thieno[2,3-b]pyrrol-4-yl)acetate (General Procedure D)

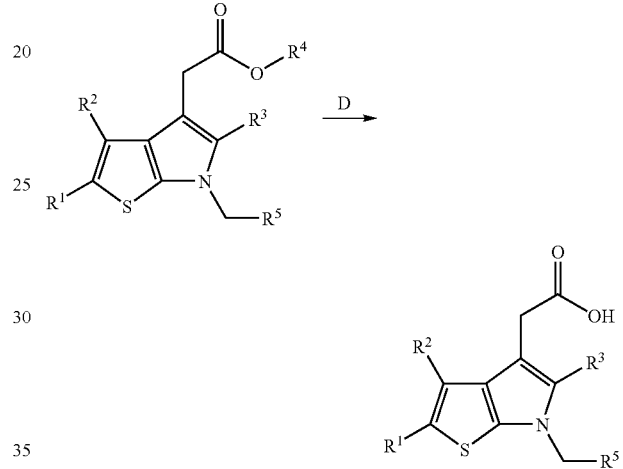

Scheme 5. Saponification of a thiophene-2-carboxylate (General Procedure E)

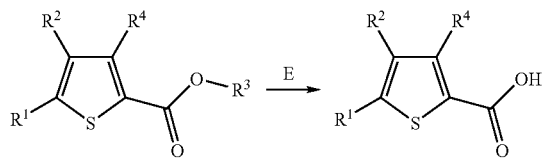

Scheme 6. Formation of a tert-butyl thiophen-2-ylcarbamate (General Procedure F)

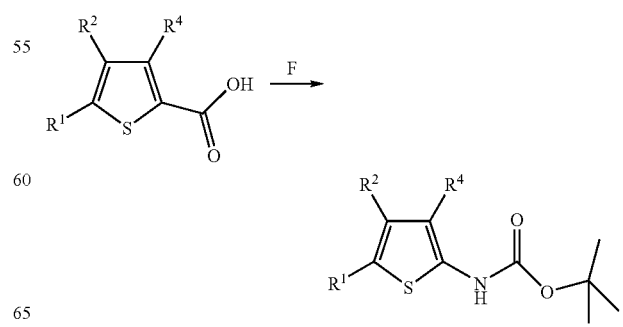

Scheme 7. Bromination of a tert-butyl thiophen-2-ylcarbamate (General Procedure G)

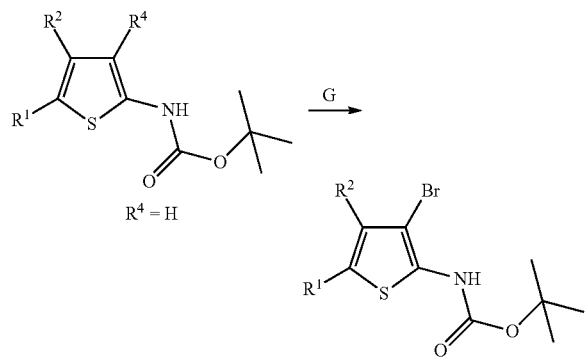

Scheme 8. One pot alkylation/cyclization to a tert-butyl 6H-thieno[2,3-b]pyrrole-6-carboxylate (General Procedure H)

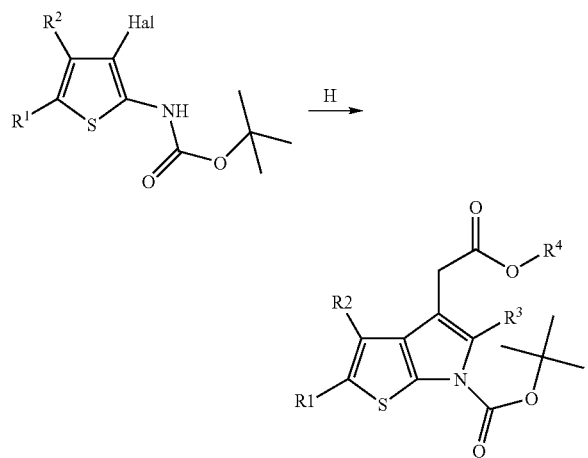

Scheme 9. Deprotection of a tert-butyl 6H-thieno[2,3-b]pyrrole-6-carboxylate (General Procedure I)

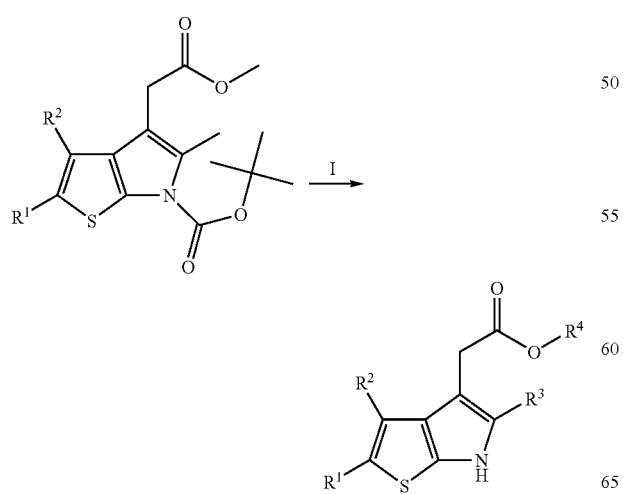

Scheme 10. Preparation of 4-(halomethyl)benzenesulfonamides (General Procedure J)

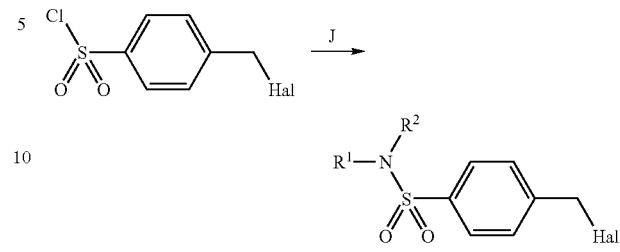

Scheme 11. Coupling of a 4H-thieno[3,2-b]pyrroles with sulfonylchlorides (General Procedure K)

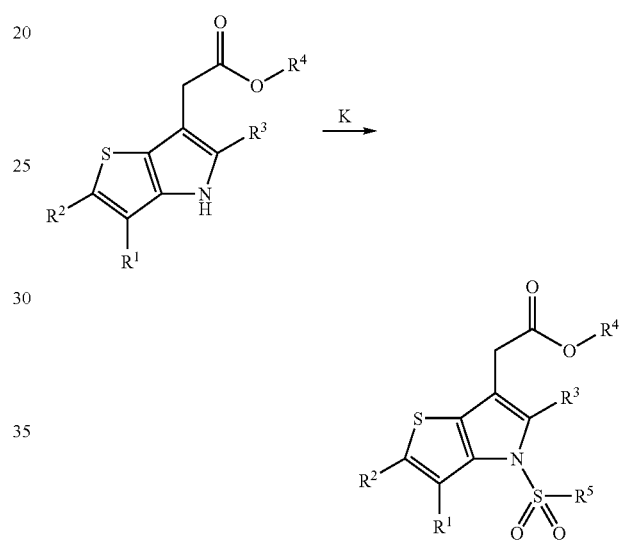

Scheme 12. Saponification of a 2-(4-(sulfonyl)-4H-thieno[3,2-b]pyrrol-6-yl)acetate 2 (General Procedure L)

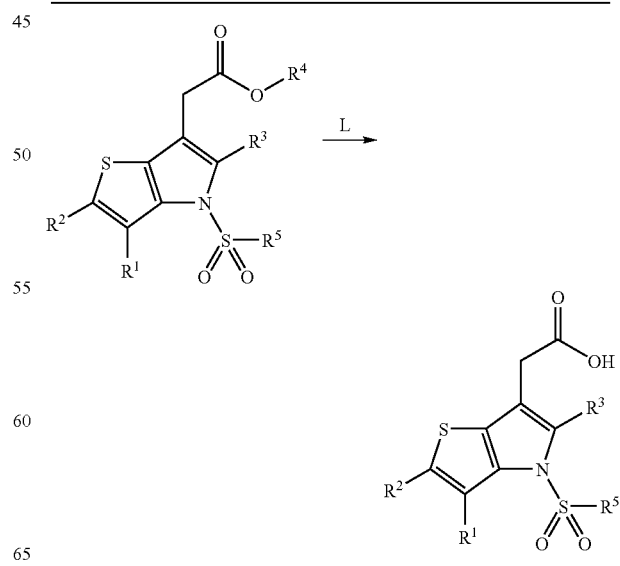

List of General Procedures

| | |
|---|---|
| General Procedure A | Coupling of a 2-(6H-thieno[2,3-b]pyrrol-4-yl)acetate with sulfonylchlorides |
| General Procedure B | Coupling of a 2-(6H-thieno[2,3-b]pyrrol-4-yl)acetate with benzylhalides |
| General Procedure C | Saponification of a 2-(6-(sulfonyl)-6H-thieno[2,3-b]pyrrol-4-yl)acetate |
| General Procedure D | Saponification of a 2-(6-benzyl-6H-thieno[2,3-b]pyrrol-4-yl)acetate |
| General Procedure E | Saponification of a thiophene-2-carboxylate |
| General Procedure F | Formation of a tert-butyl thiophen-2-ylcarbamate |
| General Procedure G | Bromination of a tert-butyl thiophen-2-ylcarbamate |
| General Procedure H | One pot alkylation/cyclization to a tert-butyl 6H-thieno[2,3-b]pyrrole-6-carboxylate |
| General Procedure I | Deprotection of a tert-butyl 6H-thieno[2,3-b]pyrrole-6-carboxylate |
| General Procedure J | Preparation of 4-(halomethyl)benzenesulfonamides |
| General Procedure K | Coupling of a 4H-thieno[3,2-b]pyrrole with sulfonylchlorides |
| General Procedure L | Saponification of a 2-(4-(sulfonyl)-4H-thieno[3,2-b]pyrrol-6-yl)acetate |

The synthetic routes to any novel intermediates are detailed by sequentially listing the general procedure (letter codes) in parentheses after their name. A worked example of this protocol is given below using Example #D.1.1 as a non-limiting illustration. Example #D.1.1 is the 5-methyl-6-(4-(methylsulfonyl)benzyl)-6H-thieno[2,3-b]pyrrol-4-yl)acetic acid which was prepared from the methyl 2-(5-methyl-6H-thieno[2,3-b]pyrrol-4-yl)acetate using General Procedure B and General Procedure D, as represented in the following synthetic scheme:

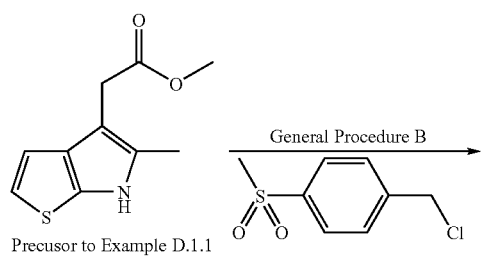

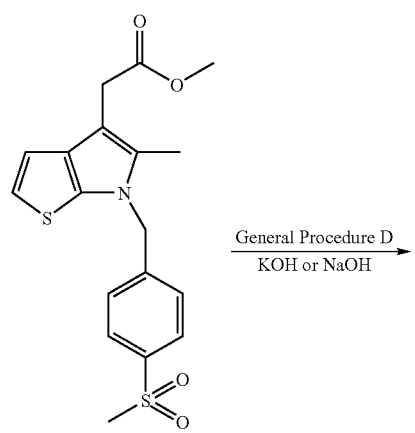

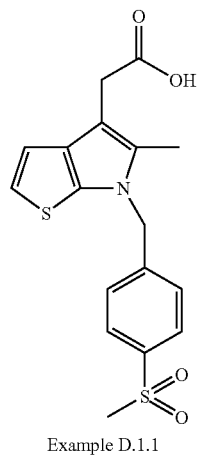

Example D.1.1

The precursor to Example #D.1.1, the methyl 2-(5-methyl-6H-thieno[2,3-b]pyrrol-4-yl)acetate, was prepared by the noted reaction sequence: using General Procedure F from the 3-bromothiophene-2-carboxylic acid with diphenylphosphoryl azide in tert-butanol, General Procedure H with the (E)-methyl 4-bromopent-2-enoate (prepared according to C. Girard, I. Romain, M. Ahmar and R. Bloch, *Tetrahedron Letters,* 1989, 30 (52), 7275), K$_2$CO$_3$, triphenylphosphine and palladium acetate, and finally deprotected by heating under vacuum according to General Procedure I, which translates to the following synthetic scheme:

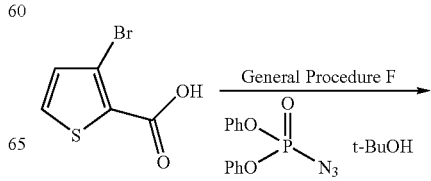

-continued

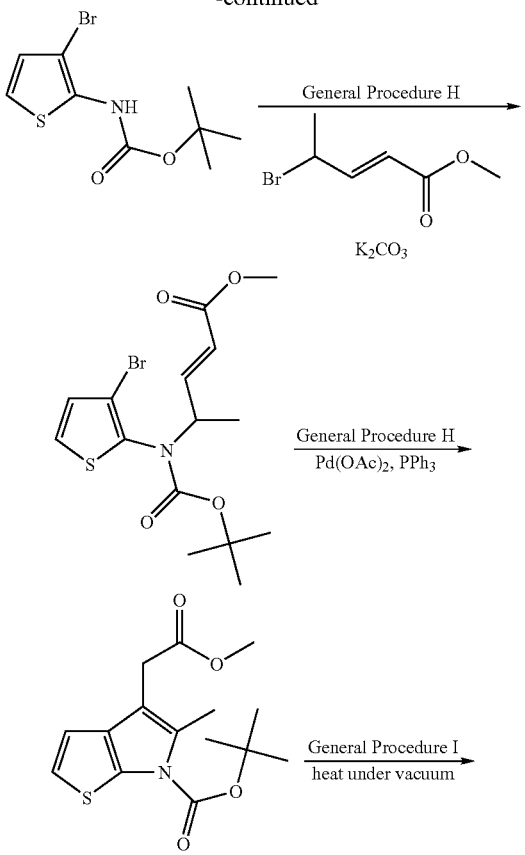

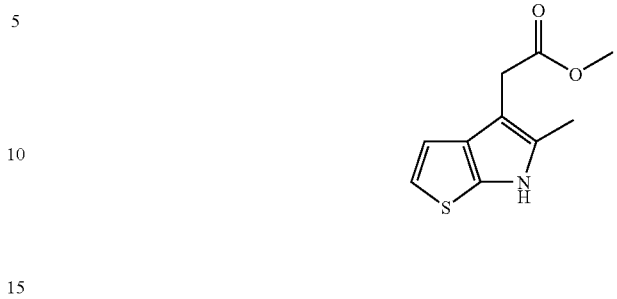

The general synthetic methods used in each general procedure follow and include an illustration of a compound that was synthesized using the designated general procedure. None of the specific conditions and reagents noted in the following are to be construed as limiting the scope of the invention and are provided for illustrative purposes only. All starting materials are commercially available from Sigma-Aldrich unless otherwise noted after the chemical name. Analytical data is included either in the illustrations of the general procedures or in the tables of examples. Unless otherwise stated, all $^1$H NMR data were collected on a Varian Mercury Plus 400 MHz instrument; chemical shifts are quoted in parts per million (ppm). LC/MS and HPLC data is referenced to the table of LC/MS and HPLC conditions using the lower case method letter in parentheses provided in Table 1.

TABLE 1

LC/MS and HPLC methods

| Method | Conditions |
|---|---|
| a | LC/MS: The column used for the chromatography was a 50 × 4.6 mm Zorbax XDB C18 column (5 µm particles). The gradient was 5-95% B in 3.7 min with a hold at 95% B for 1 min (1.3 mL/min flow rate). Mobile phase A was 10 mM ammonium acetate and mobile phase B was HPLC grade acetonitrile. Detection methods are diode array (DAD) and evaporative light scattering (ELSD) detection as well as positive/negative electrospray ionization |
| b | LC/MS: The column used for the chromatography was a 50 × 4.6 mm Zorbax XDB C18 column (5 µm particles). The gradient was 5-95% B in 3.7 min with a hold at 95% B for 1 min (1.3 mL/min flow rate). Mobile phase A was 10 mM ammonium acetate, mobile phase B was HPLC grade acetonitrile. Detection methods are diode array (DAD) and evaporative light scattering (ELSD) detection as well as pos/neg atmospheric pressure chemical ionization (APCI). |
| c | LC/MS: The column used for the chromatography was a 4.6 × 30 mm Vydac Genesis C8 column (4 µm particles). The gradient was 5-60% B in 1.5 min then 60-95% B to 2.5 min with a hold at 95% B for 1.2 min (1.3 mL/min flow rate). Mobile phase A was 10 mM ammonium acetate and mobile phase B was HPLC grade acetonitrile. Detection methods are diode array (DAD) and evaporative light scattering (ELSD) detection as well as positive/negative electrospray ionization. |
| d | LC/MS: The column used for the chromatography was a 4.6 × 30 mm Vydac Genesis C8 column (4 µm particles). The gradient was 30-95% B in 2 min then hold at 95% B to 5.7 min (1.0 mL/min flow rate). Mobile phase A was 10 mM ammonium acetate and mobile phase B was HPLC grade acetonitrile. Detection methods are diode array (DAD) and evaporative light scattering (ELSD) detection as well as positive/negative electrospray ionization. |
| e | LC-MS: Using a Waters ZMD mass spectrometer and Alliance HPLC system running MassLynx 3.4 and Openlynx 3.4 software. The ZMD mass spectrometer was operated under positive APCI ionization conditions. The HPLC system comprised a Waters 2795 autosampler sampling from 96-well plates, a Waters 996 diode-array detector and Sedere Sedex-75 evaporative light scattering detector. The column used was a Phenomenex Luna Combi-HTS C8(2) 5 µm 100Å (2.1 mm × 30 mm). A gradient of 10-100% acetonitrile (A) and 0.1% trifluoroacetic acid in water (B) was used, at a flow rate of 1.5 mL/min (0-0.1 min 10% A, 0.1-3.1 min 10-100% A, 3.1-3.9 min 100-10% A, 3.9-4.0 min 100-10% A). |

TABLE 1-continued

LC/MS and HPLC methods

| Method | Conditions |
|---|---|
| f | HPLC: The column used for the chromatography was a 21.2 × 250 mm Hypersil C18 HS column (8 μm particles). The gradient was 15-100% B over 25 min (21 mL/min flow rate). Mobile phase A was 0.05 N aqueous ammonium acetate buffer (pH 4.5) and mobile phase B was HPLC grade acetonitrile. Detection method is UV, λ = 254 nm. |
| g | HPLC: The column used for the chromatography was a 21.2 × 250 mm Hypersil C18 HS column (8 μm particles). The gradient was 0-80% B over 50 min (21 mL/min flow rate). Mobile phase A was 0.05 N aqueous ammonium acetate buffer (pH 4.5) and mobile phase B was HPLC grade acetonitrile. Detection method is UV, λ = 254 nm. |
| h | HPLC: The column used for the chromatography was a 21.2 × 250 mm Hypersil C18 HS column (8 μm particles). The gradient was 5-95% B over 25 min (21 mL/min flow rate). Mobile phase A was 0.05N aqueous ammonium acetate buffer (pH 4.5) and mobile phase B was HPLC grade acetonitrile. Detection method is UV, λ = 254 nm. |
| g | HPLC: The column used for the chromatography was a 21.2 × 250 mm Hypersil C18 HS column (8 μm particles). The gradient was 5-100% B over 25 min (21 mL/min flow rate). Mobile phase A was 0.05N aqueous ammonium acetate buffer (pH 4.5) and mobile phase B was HPLC grade acetonitrile. Detection method is UV, λ = 254 nm. |
| h | HPLC on a Waters Nova-Pak ® HR C18 6um 60 Å Prep-Pak ® cartridge column (25 mm × 100 mm). A gradient of acetonitrile (A) and 0.1% trifluoroacetic acid in water (B) was used, at a flow rate of 40 mL/min (0-0.5 min 10% A, 0.5-6.0 min linear gradient 10-100% A, 6.0-7.0 min 100% A, 7.0-8.0 min linear gradient 100-10% A). Samples were injected in 1.5 mL DMSO:MeOH (1:1). An Agilent 1100 Series Purification system was used, consisting of the following modules: Agilent 1100 Series LC/MSD SL mass spectrometer with API-electrospray source; two Agilent 1100 Series preparative pumps; Agilent 1100 Series isocratic pump; Agilent 1100 Series diode array detector with preparative (0.3 mm) flow cell; Agilent 35900E multichannel interface; LC-Packings Acurate 1: 1000 flow-splitter; Gilson 215 liquid-handler with 819 Injector fitted with a 2 mL loop; and Sedere Sedex-55 evaporative light scattering detector (ELSD). The make-up pump for the mass spectrometer used 3:1 methanol:water with 0.1% formic acid at a flow rate of 1 mL/min. A tee downstream of the flow-splitter divided the flow between ELSD and MS detectors with 0.45 mL/min flow to the MS. Fraction collection was automatically triggered when the extracted ion chromatogram (EIC) for the target mass exceeded the threshold specified in the method. The system was controlled using Agilent Chemstation (Rev A.08.04) and Integ CC-Mode (Rev A.03.02) software, with custom Chemstation macros for data export |

General Procedure A: Coupling of a 2-(6H-thieno[2,3-b]pyrrol-4-yl)acetate with sulfonylchlorides To a solution of alkyl 2-(6H-thieno[2,3-b]pyrrol-4-yl)acetate (such as methyl, ethyl or tert-butyl, preferably methyl 2-(6H-thieno[2,3-b]pyrrol-4-yl)acetate) (preferably 1 equiv) in an organic solvent (such as THF or dioxane, preferably THF) at about −5° C. to 25° C. (preferably 0° C.) is added a base (such as potassium tBuOK, tBuONa, NaOEt, NaOMe, preferably tBuOK) (1-2 equiv, preferably 1.4 equiv), followed by a sulfonyl chloride (1-1.5 equiv, preferably 1.2 equiv). The reaction mixture is stirred at ambient temperature for about 30 min-2 h (preferably 1 h) to give the crude 2-(6-(sulfonyl)-6H-thieno[2,3-b]pyrrol-4-yl)acetate, which can be used in subsequent reactions without further purification. Illustration of General Procedure Preparation #A.1: Methyl 2-(5-methyl-6-(4-(methylsulfonyl)phenylsulfonyl)-6H-thieno[2,3-b]pyrrol-4-yl)acetate

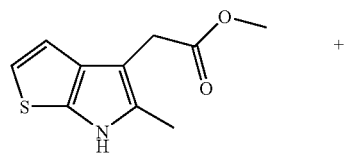
+

-continued

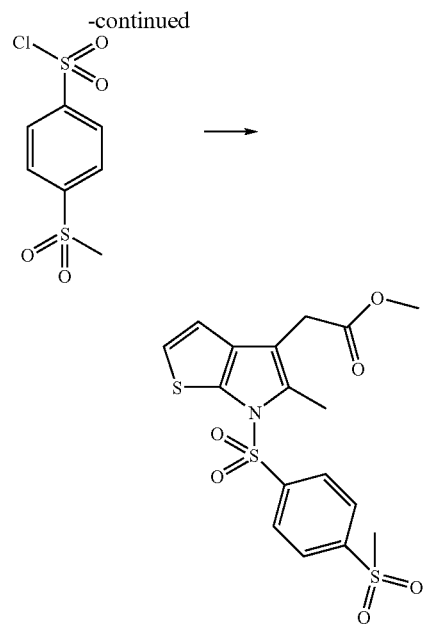

To a solution of methyl 2-(5-methyl-6H-thieno[2,3-b]pyrrol-4-yl)acetate (0.059 g, 0.282 mmol) in THF at about 0° C. was added tBuOK (0.044 g, 0.395 mmol), followed by the 4-(methylsulfonyl)-benzene-1-sulfonyl chloride (0.086 g, 0.338 mmol). The reaction mixture was stirred at ambient temperature for about 1 h to give the crude title compound, which was used without further purification. LC/MS (Table 1, Method b) $R_t$=2.25 min; MS m/z 428 (M+H)$^+$.

General Procedure B: Coupling of a 2-(6H-thieno[2,3-b]pyrrol-4-yl)acetate with benzylhalides Sodium hydride (1-2 equiv, preferably 1.12 equiv) is added to a solution of alkyl 2-(6H-thieno[2,3-b]pyrrol-4-yl)acetate (such as methyl, ethyl or tert-butyl, preferably methyl 2-(6H-thieno[2,3-b]pyrrol-4-yl)acetate) (preferably 1 equiv) in an organic solvent (such as DMF, THF or dioxane, preferably DMF) at about 0-10° C. (preferably about 0° C.). The mixture is stirred at about 0-10° C. (preferably about 0° C.) for about 1-5 h (preferably about 1 h) before sequential addition of a benzyl halide (1-2 equiv, preferably 1.2 equiv) and sodium iodide (1-2 equiv, preferably 1.2 equiv). The resulting reaction mixture is allowed to warm up to ambient temperature over about 2-10 h (preferably 4 h). The crude mixture is diluted with an organic solvent (such as EtOAc, DCM or Et$_2$O, preferably EtOAc) and washed with water. The layers are separated and the organic solution is dried over a drying agent (such as Na$_2$SO$_4$ or MgSO$_4$, preferably MgSO$_4$), filtered and concentrated under reduced pressure to give the target compound, which can optionally be purified by chromatography on silica gel.
Illustration of General Procedure B Preparation #B.1: Methyl 2-(5-methyl-6-(4-(methylsulfonyl)benzyl)-6H-thieno[2,3-b]pyrrol-4-yl)acetate

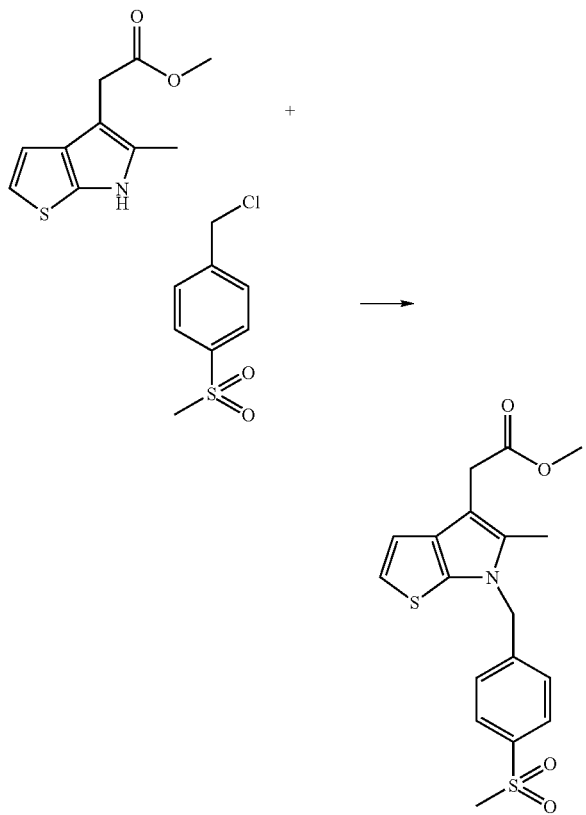

Sodium hydride (0.014 g, 0.583 mmol) was added to a solution of methyl 2-(5-methyl-6H-thieno[2,3-b]pyrrol-4-yl)acetate (0.109 g, 0.52 mmol) in DMF (5 mL) at 0° C. The mixture was stirred 1 h at 0° C. before sequential addition of the 1-(chloromethyl)-4-(methylsulfonyl)benzene (0.156 g, 0.762 mmol) and sodium iodide (0.0935 g, 0.624 mmol). The reaction mixture was allowed to warm up to ambient temperature over 4 h. EtOAc was added and the resulting solution washed with water. The layers were separated and the organic solution was dried over MgSO$_4$, filtered and concentrated under reduced pressure. The crude material was purified by chromatography on silica gel (heptane/EtOAc: 80/20 to 50/50) to give the title compound (0.117 g, 59.6%): LC/MS (Table 1, Method b) $R_t$=2.45 min; MS m/z 395 (M+NH$_4$)$^+$.

General Procedure C: Saponification of a 2-(6-(sulfonyl)-6H-thieno[2,3-b]pyrrol-4-yl)acetate To a 2-(6-(sulfonyl)-6H-thieno[2,3-b]pyrrol-4-yl)acetate (1 equiv) in an organic solvent (such as THF or dioxane, preferably THF) is added an alcohol (such as MeOH or EtOH, preferably EtOH) (20-50 equiv, preferably 40 equiv) and water, followed by a base (such as NaOH, KOH or LiOH preferably KOH) (2-5 equiv, preferably 3 equiv). The reaction mixture is stirred at ambient temperature for about 10 min-4 h (preferably 2 h). An acid (such as HCOOH, TFA, AcOH, preferably AcOH) (2-5 equiv, preferably 3 equiv) is added. The reaction mixture is dried under reduced pressure (Genevac®) and the residue purified by preparative HPLC.
Illustration of General Procedure C Example C.1.1: 2-(5-Methyl-6-(4-(methylsulfonyl)phenylsulfonyl)-6H-thieno[2,3-b]pyrrol-4-yl)acetic acid

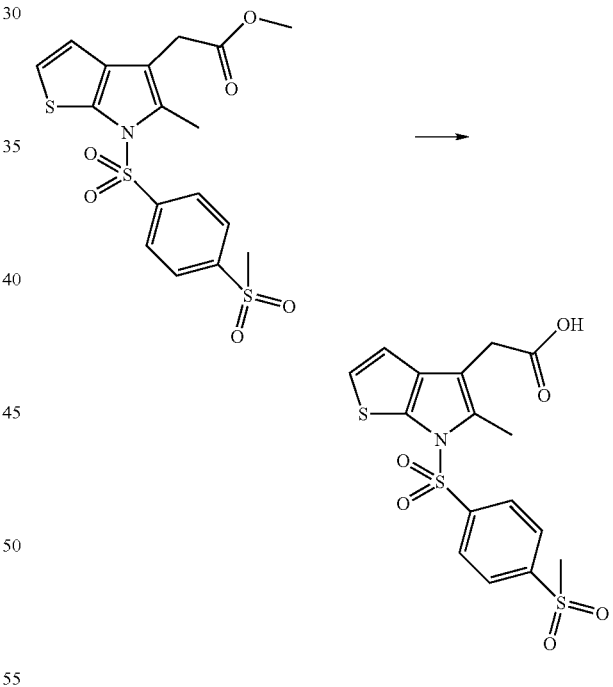

Methanol (0.5 mL) and water (0.5 mL) were added to the crude methyl 2-(5-methyl-6-(4-(methylsulfonyl)phenylsulfonyl)-6H-thieno[2,3-b]pyrrol-4-yl)acetate, followed by the addition of KOH (47.5 mg, 0.846 mmol). The mixture was stirred at ambient temperature for 1 h before adding the AcOH (0.66 mL). The reaction mixture was dried under reduced pressure (Genevac®) and the residue purified by HPLC (Table 1, Method g) to afford the title compound (0.017 g, 14.6%): LC/MS (Table 1, Method b) $R_t$=1.89 min; MS m/z 412 (M−H)$^-$; $^1$H NMR (DMSO) δ 8.19-8.08 (m, 4H), 7.23 (d, 1H, J=5.28 Hz), 6.96 (d, 1H, J=5.28 Hz), 3.41 (s, 2H), 3.29 (s, 3H), 2.37 (s, 3H).

TABLE C.1

Examples of 2-(6-sulfonyl-5-methyl-6H-thieno[2,3-b]pyrrol-4-yl)acetic acids
General Procedure C

| Ester | Product | Example # | R$_t$ min (method) | m/z ESI |
|---|---|---|---|---|
| Methyl 2-(5-methyl-6-(phenylsulfonyl)-6H-thieno[2,3-b]pyrrol-4-yl)acetate [prepared using A from the methyl 2-(5-methyl-6H-thieno[2,3-b]pyrrol-4-yl)acetate and the benzenesulfonyl chloride] | 2-(5-Methyl-6-(phenylsulfonyl)-6H-thieno[2,3-b]pyrrol-4-yl)acetic acid | C.1.2 | 2.03 (b) | 336.1 (M + H)$^+$ |
| Methyl 2-(5-methyl-6-(phenylsulfonyl)-6H-thieno[2,3-b]pyrrol-4-yl)acetate [prepared using A from the methyl 2-(5-methyl-6H-thieno[2,3-b]pyrrol-4-yl)acetate and the 4-chlorobenzene-1-sulfonyl chloride] | 2-(6-(4-Chlorophenylsulfonyl)-5-methyl-6H-thieno[2,3-b]pyrrol-4-yl)acetic acid | C.1.3 | 2.07 (b) | 370.0 (M + H)$^+$ |
| Methyl 2-(5-methyl-6-(phenylsulfonyl)-6H-thieno[2,3-b]pyrrol-4-yl)acetate [prepared using A from the methyl 2-(5-methyl-6H-thieno[2,3-b]pyrrol-4-yl)acetate and the naphthalene-1-sulfonyl chloride] | 2-(5-Methyl-6-(naphthalen-1-ylsulfonyl)-6H-thieno[2,3-b]pyrrol-4-yl)acetic acid | C.1.4 | 2.19 (b) | 386.1 (M + H)$^+$ |
| Methyl 2-(5-methyl-6-(phenylsulfonyl)-6H-thieno[2,3-b]pyrrol-4-yl)acetate [prepared using A from the methyl 2-(5-methyl-6H-thieno[2,3-b]pyrrol-4-yl)acetate and the 4-(trifluoromethyl)benzene-1-sulfonyl chloride] | 2-(5-Methyl-6-(4-(trifluoromethyl)phenylsulfonyl)-6H-thieno[2,3-b]pyrrol-4-yl)acetic acid | C.1.5 | 2.24 (b) | 404.1 (M + H)$^+$ |
| Methyl 2-(5-methyl-6-(phenylsulfonyl)-6H-thieno[2,3-b]pyrrol-4-yl)acetate [prepared using A from the methyl 2-(5-methyl-6H-thieno[2,3-b]pyrrol-4-yl)acetate and the 3,4-dichlorobenzene-1-sulfonyl chloride] | 2-(6-(3,4-Dichlorophenylsulfonyl)-5-methyl-6H-thieno[2,3-b]pyrrol-4-yl)acetic acid | C.1.6 | 2.30 (b) | 403.0 (M − H)$^-$ |
| Methyl 2-(5-methyl-6-(phenylsulfonyl)-6H-thieno[2,3-b]pyrrol-4-yl)acetate [prepared using A from the methyl 2-(5-methyl-6H-thieno[2,3-b]pyrrol-4-yl)acetate and the 2,5-dichlorobenzene-1-sulfonyl chloride] | 2-(6-(2,5-Dichlorophenylsulfonyl)-5-methyl-6H-thieno[2,3-b]pyrrol-4-yl)acetic acid | C.1.7 | 2.20 (b) | 403.0 (M − H)$^-$ |
| Methyl 2-(5-methyl-6-(phenylsulfonyl)-6H-thieno[2,3-b]pyrrol-4-yl)acetate [prepared using A from the methyl 2-(5-methyl-6H-thieno[2,3-b]pyrrol-4-yl)acetate and the 3,5-dichlorobenzene-1-sulfonyl chloride] | 2-(6-(3,5-Dichlorophenylsulfonyl)-5-methyl-6H-thieno[2,3-b]pyrrol-4-yl)acetic acid | C.1.8 | 2.28 (b) | 403.0 (M − H)$^-$ |
| Methyl 2-(5-methyl-6-(phenylsulfonyl)-6H-thieno[2,3-b]pyrrol-4-yl)acetate [prepared using A from the methyl 2-(5-methyl-6H-thieno[2,3-b]pyrrol-4-yl)acetate and the 2,3-dichlorobenzene-1-sulfonyl chloride] | 2-(6-(2,3-Dichlorophenylsulfonyl)-5-methyl-6H-thieno[2,3-b]pyrrol-4-yl)acetic acid | C.1.9 | 2.20 (b) | 403.0 (M − H)$^-$ |
| Methyl 2-(5-methyl-6-(phenylsulfonyl)-6H-thieno[2,3-b]pyrrol-4-yl)acetate [prepared using A from the methyl 2-(5-methyl-6H-thieno[2,3-b]pyrrol-4-yl)acetate and the 4-fluorobenzene-1-sulfonyl chloride] | 2-(6-(4-Fluorophenylsulfonyl)-5-methyl-6H-thieno[2,3-b]pyrrol-4-yl)acetic acid | C.1.10 | 2.07 (b) | 354.1 (M + H)$^+$ |
| Methyl 2-(5-methyl-6-(phenylsulfonyl)-6H-thieno[2,3-b]pyrrol-4-yl)acetate [prepared using A from the methyl 2-(5- | 2-(5-Methyl-6-(4-(morpholinosulfonyl)phenylsulfonyl)-6H-thieno[2,3-b]pyrrol-4-yl)acetic acid | C.1.11 | 2.10 (b) | 483.1 (M − H)$^-$ |

TABLE C.1-continued

Examples of 2-(6-sulfonyl-5-methyl-6H-thieno[2,3-b]pyrrol-4-yl)acetic acids
General Procedure C

| Ester | Product | Example # | $R_t$ min (method) | m/z ESI |
|---|---|---|---|---|
| methyl-6H-thieno[2,3-b]pyrrol-4-yl)acetate and the 4-(morpholmosulfonyl)benzene-1-sulfonyl chloride [Matrix]] | | | | |
| Methyl 2-(5-methyl-6-(phenylsulfonyl)-6H-thieno[2,3-b]pyrrol-4-yl)acetate [prepared using A from the methyl 2-(5-methyl-6H-thieno[2,3-b]pyrrol-4-yl)acetate and the 4-(pyrrolidin-1-ylsulfonyl)benzene-1-sulfonyl chloride [Matrix]] | 2-(5-Methyl-6-(4-(pyrrolidin-1-ylsulfonyl)phenylsulfonyl)-6H-thieno[2,3-b]pyrrol-4-yl)acetic acid | C.1.12 | 2.10 (b) | 467.1 (M − H)− |
| Methyl 2-(5-methyl-6-(phenylsulfonyl)-6H-thieno[2,3-b]pyrrol-4-yl)acetate [prepared using A from the methyl 2-(5-methyl-6H-thieno[2,3-b]pyrrol-4-yl)acetate and the pyridine-3-sulfonyl chloride [Matrix]] | 2-(5-Methyl-6-(pyridin-3-ylsulfonyl)-6H-thieno[2,3-b]pyrrol-4-yl)acetic acid | C.1.13 | 1.80 (b) | 337.1 (M + H)+ |
| Methyl 2-(5-methyl-6-(phenylsulfonyl)-6H-thieno[2,3-b]pyrrol-4-yl)acetate [prepared using A from the methyl 2-(5-methyl-6H-thieno[2,3-b]pyrrol-4-yl)acetate and the 4-cyanobenzene-1-sulfonyl chloride] | 2-(6-(4-Cyanophenylsulfonyl)-5-methyl-6H-thieno[2,3-b]pyrrol-4-yl)acetic acid | C.1.14 | 2.00 (b) | 359.0 (M − H)− |
| Methyl 2-(5-methyl-6-(phenylsulfonyl)-6H-thieno[2,3-b]pyrrol-4-yl)acetate [prepared using A from the methyl 2-(5-methyl-6H-thieno[2,3-b]pyrrol-4-yl)acetate and the 4-(3,3-dimethylureido)benzene-1-sulfonyl chloride [Oakwood Products Inc]] | 2-(6-(4-(3,3-Dimethylureido)phenylsulfonyl)-5-methyl-6H-thieno[2,3-b]pyrrol-4-yl)acetic acid | C.1.15 | 1.80 (b) | 422.1 (M + H)+ |
| Methyl 2-(5-methyl-6-(phenylsulfonyl)-6H-thieno[2,3-b]pyrrol-4-yl)acetate [prepared using A from the methyl 2-(5-methyl-6H-thieno[2,3-b]pyrrol-4-yl)acetate and the 4-acetamidobenzene-1-sulfonyl chloride] | 2-(6-(4-Acetamidophenylsulfonyl)-5-methyl-6H-thieno[2,3-b]pyrrol-4-yl)acetic acid | C.1.16 | 1.90 (b) | 393.1 (M + H)+ |

TABLE C.2

Examples of 2-(6-(sulfonyl)-6H-thieno[2,3-b]pyrrol-4-yl)acetic acid prepared
using General Procedure C

| Ester | Product | Example # | $R_t$ min (method) | m/z ESI |
|---|---|---|---|---|
| Ethyl 2-(6-(4-(methylsulfonyl)phenylsulfonyl)-6H-thieno[2,3-b]pyrrol-4-yl)acetate [prepared using A from ethyl 2-(6H-thieno[2,3-b]pyrrol-4-yl)acetate and 4-(methylsulfonyl)benzene-1-sulfonyl chloride] | 2-(6-(4-(Methylsulfonyl)phenylsulfonyl)-6H-thieno[2,3-b]pyrrol-4-yl)acetic acid | C.2.1 | 2.66 (a) | 398.2 (M − H)− |
| Ethyl 2-(6-(4-chlorophenylsulfonyl)-6H-thieno[2,3-b]pyrrol-4-yl)acetate [prepared using A from ethyl 2-(6H-thieno[2,3-b]pyrrol-4-yl)acetate and 4-chlorobenzene-1-sulfonyl chloride] | 2-(6-(4-Chlorophenylsulfonyl)-6H-thieno[2,3-b]pyrrol-4-yl)acetic acid | C.2.2 | 3.12 (a) | 354.2 (M − H)− |

TABLE C.2-continued

Examples of 2-(6-(sulfonyl)-6H-thieno[2,3-b]pyrrol-4-yl)acetic acid prepared using General Procedure C

| Ester | Product | Example # | $R_t$ min (method) | m/z ESI |
|---|---|---|---|---|
| Ethyl 2-(6-(2,5-dichlorophenylsulfonyl)-6H-thieno[2,3-b]pyrrol-4-yl)acetate [prepared using A from ethyl 2-(6H-thieno[2,3-b]pyrrol-4-yl)acetate and 2,5-dichlorobenzene-1-sulfonyl chloride] | 2-(6-(2,5-Dichlorophenylsulfonyl)-6H-thieno[2,3-b]pyrrol-4-yl)acetic acid | C.2.3 | 3.29 (a) | 390.1 (M + H)$^+$ |

TABLE C.3

Examples of 2-(3,5-dimethyl-6-(sulfonyl)-6H-thieno[2,3-b]pyrrol-4-yl)acetic acid using General Procedure C

| Ester | Product | Example # | $R_t$ min (method) | m/z ESI |
|---|---|---|---|---|
| Methyl 2-(6-(3,5-dichlorophenylsulfonyl)-3,5-dimethyl-6H-thieno[2,3-b]pyrrol-4-yl)acetate [prepared using A from the methyl 2-(3,5-dimethyl-6H-thieno[2,3-b]pyrrol-4-yl)acetate and the 3,5-dichlorobenzene-1-sulfonyl chloride] | 2-(6-(3,5-Dichlorophenylsulfonyl)-3,5-dimethyl-6H-thieno[2,3-b]pyrrol-4-yl)acetic acid | C.3.1 | 2.39 (a) | 416.0 (M − H)$^-$ |
| Methyl 2-(6-(4-fluorophenylsulfonyl)-3,5-dimethyl-6H-thieno[2,3-b]pyrrol-4-yl)acetate [prepared using A from the methyl 2-(3,5-dimethyl-6H-thieno[2,3-b]pyrrol-4-yl)acetate and the 4-fluorobenzene-1-sulfonyl chloride] | 2-(6-(4-Fluorophenylsulfonyl)-3,5-dimethyl-6H-thieno[2,3-b]pyrrol-4-yl)acetic acid | C.3.2 | 2.16 (a) | 366.0 (M − H)$^-$ |
| Methyl 2-(3,5-dimethyl-6-(4-(methylsulfonyl)phenylsulfonyl)-6H-thieno[2,3-b]pyrrol-4-yl)acetate [prepared using A from the methyl 2-(3,5-dimethyl-6H-thieno[2,3-b]pyrrol-4-yl)acetate and the 4-(methylsulfonyl)benzene-1-sulfonyl chloride] | 2-(3,5-Dimethyl-6-(4-(methylsulfonyl)phenylsulfonyl)-6H-thieno[2,3-b]pyrrol-4-yl)acetic acid | C.3.3 | 1.96 (b) | 426.0 (M − H)$^-$ |
| Methyl 2-(3,5-dimethyl-6-(4-(methylsulfonyl)phenylsulfonyl)-6H-thieno[2,3-b]pyrrol-4-yl)acetate [prepared using A from the methyl 2-(3,5-dimethyl-6H-thieno[2,3-b]pyrrol-4-yl)acetate and the 4-benzenesulfonyl chloride] | 2-(3,5-Dimethyl-6-(phenylsulfonyl)-6H-thieno[2,3-b]pyrrol-4-yl)acetic acid | C.3.4 | 2.09 (b) | 350.1 (M + H)$^+$ |
| Methyl 2-(3,5-dimethyl-6-(4-(methylsulfonyl)phenylsulfonyl)-6H-thieno[2,3-b]pyrrol-4-yl)acetate [prepared using A from the methyl 2-(3,5-dimethyl-6H-thieno[2,3-b]pyrrol-4-yl)acetate and the 4-chlorobenzene-1-sulfonyl chloride] | 2-(6-(4-Chlorophenylsulfonyl)-3,5-dimethyl-6H-thieno[2,3-b]pyrrol-4-yl)acetic acid | C.3.5 | 2.40 (b) | 384.0 (M + H)$^+$ |
| Methyl 2-(3,5-dimethyl-6-(4-(methylsulfonyl)phenylsulfonyl)-6H-thieno[2,3-b]pyrrol-4-yl)acetate [prepared using A from the methyl 2-(3,5-dimethyl-6H-thieno[2,3-b]pyrrol-4-yl)acetate and the naphthalene-1-sulfonyl chloride] | 2-(3,5-Dimethyl-6-(naphthalen-1-ylsulfonyl)-6H-thieno[2,3-b]pyrrol-4-yl)acetic acid | C.3.6 | 2.26 (b) | 400.1 (M + H)$^+$ |
| Methyl 2-(3,5-dimethyl-6-(4-(methylsulfonyl)phenylsulfonyl)-6H-thieno[2,3-b]pyrrol-4-yl)acetate [prepared using A from the methyl 2-(3,5-dimethyl-6H-thieno[2,3-b]pyrrol-4-yl)acetate and the 4-(trifluoromethyl)benzene-1-sulfonyl chloride] | 2-(3,5-Dimethyl-6-(4-(trifluoromethyl)phenylsulfonyl)-6H-thieno[2,3-b]pyrrol-4-yl)acetic acid | C.3.7 | 2.28 (b) | 418.2 (M + H)$^+$ |

General Procedure D: Saponification of a 2-(6-benzyl-6H-thieno[2,3-b]pyrrol-4-yl)acetate An aqueous solution of a base (such as NaOH, KOH or LiOH, preferably NaOH) (1-4 mol/L, preferably 1 mol/L) (2-5 equiv, preferably 2 equiv) is added to a solution of alkyl 2-(6-benzyl-5-methyl-6H-thieno[2,3-b]pyrrol-4-yl)acetate (1 equiv) in an organic solvent such (MeOH, EtOH, preferably MeOH). The reaction mixture is stirred at about ambient temperature for about 1-5 h (preferably 3 h). The mixture is diluted with an organic solvent (such as EtOAc, DCM or Et$_2$O, preferably DCM) and washed with water. The aqueous extracts are acidified to pH about 1-3 (preferably pH=3) with a 1N aqueous solution of hydrochloric acid and extracted with an organic solvent (such as EtOAc, DCM or Et$_2$O, preferably DCM). The layers are separated and the organic solution is dried over a drying agent (such as Na$_2$SO$_4$ or MgSO$_4$, preferably MgSO$_4$) filtered and concentrated under reduced pressure to give the target compound. Optionally, the product can be purified by trituration with an organic solvent such as (Et$_2$O or heptane, preferably Et$_2$O).

Illustration of General Procedure D

Example #D.1.1: 5-Methyl-6-(4-(methylsulfonyl)benzyl)-6H-thieno[2,3-b]pyrrol-4-yl)acetic acid

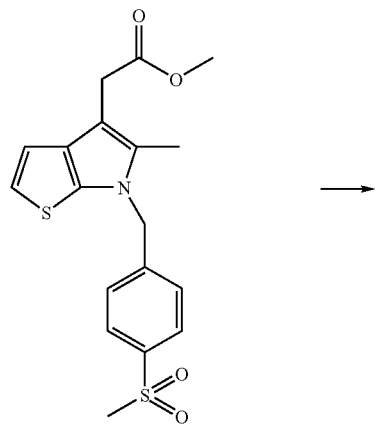

→

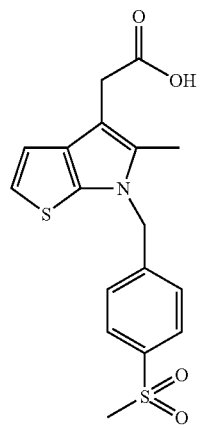

An aqueous solution of NaOH (1 mol/L, 0.620 mL, 0.620 mmol) was added to a solution of methyl 2-(5-methyl-6-(4-(methylsulfonyl)benzyl)-6H-thieno[2,3-b]pyrrol-4-yl)acetate (0.117 g, 0.310 mmol) in MeOH (3 mL). The reaction mixture was stirred at ambient temperature for 2 h. The mixture was diluted with DCM and washed with water. The aqueous extracts were acidified to about pH 3 with a 1N aqueous solution of hydrochloric acid and extracted with DCM. The layers were separated and the organic solution was dried over MgSO$_4$, filtered, and concentrated under reduced pressure to give the title compound (0.047 g, 41.7%): LC/MS (Table 1, Method a) R$_t$=2.79 min; MS m/z 381 (M+NH$_4$)$^+$; $^1$H NMR (CDCl$_3$) δ 7.88 (d, 2H, J=8.4 Hz), 7.25 (d, 2H, J=8.4 Hz), 6.99 (d, 1H, J=5.2 Hz), 6.78 (d, 1H, J=5.2 Hz), 5.21 (s, 2H), 3.66 (s, 2H), 3.03 (s, 3H), 2.26 (s, 3H).

TABLE D.1

Examples of 2-(6-benzyl-5-methyl-6H-thieno[2,3-b]pyrrol-4-yl)acetic acids prepared from using General Procedure D

| Ester | Product | Example # | R$_t$ min (method) | m/z ESI |
|---|---|---|---|---|
| Methyl 2-(6-(4-tert-butylbenzyl)-5-methyl-6H-thieno[2,3-b]pyrrol-4-yl)acetate [prepared using B from the methyl 2-(5-methyl-6H-thieno[2,3-b]pyrrol-4-yl)acetate and the 1-(bromomethyl)-4-tert-butylbenzene] | 2-(6-(4-tert-Butylbenzyl)-5-methyl-6H-thieno[2,3-b]pyrrol-4-yl)acetic acid | D.1.2 | 2.55 (b) | 342.2 (M + H)$^+$ |
| Methyl 2-(6-(4-methoxybenzyl)-5-methyl-6H-thieno[2,3-b]pyrrol-4-yl)acetate [prepared using B from the methyl 2-(5-methyl-6H-thieno[2,3-b]pyrrol-4-yl)acetate and the 1-(chloromethyl)-4-methoxybenzene] | 2-(6-(4-Methoxybenzyl)-5-methyl-6H-thieno[2,3-b]pyrrol-4-yl)acetic acid | D.1.3 | 2.00 (b) | 316.1 (M + H)$^+$ |
| Methyl 2-(6-(4-(1H-pyrazol-1-yl)benzyl)-5-methyl-6H-thieno[2,3-b]pyrrol-4-yl)acetate [prepared using B from the methyl 2-(5-methyl-6H-thieno[2,3-b]pyrrol-4-yl)acetate and the 1-(4-(bromomethyl)phenyl)-1H-pyrazole [Maybridge]] | 2-(6-(4-(1H-Pyrazol-1-yl)benzyl)-5-methyl-6H-thieno[2,3-b]pyrrol-4-yl)acetic acid | D.1.4 | 2.00 (b) | 352.1 (M + H)$^+$ |

TABLE D.1-continued

Examples of 2-(6-benzyl-5-methyl-6H-thieno[2,3-b]pyrrol-4-yl)acetic acids prepared from using General Procedure D

| Ester | Product | Example # | R_t min (method) | m/z ESI |
|---|---|---|---|---|
| Methyl 2-(6-(2-chloro-4-(methylsulfonyl)benzyl)-5-methyl-6H-thieno[2,3-b]pyrrol-4-yl)acetate [prepared using B from the methyl 2-(5-methyl-6H-thieno[2,3-b]pyrrol-4-yl)acetate and the 1-(bromomethyl)-2-chloro-4-(methylsulfonyl)benzene [Oakwood Products Inc]] | 2-(6-(2-Chloro-4-(methylsulfonyl)benzyl)-5-methyl-6H-thieno[2,3-b]pyrrol-4-yl)acetic acid | D.1.5 | 2.55 (b) | 398.0 (M + H)$^+$ |
| Methyl 2-(6-(4-(N,N-dimethylsulfamoyl)benzyl)-5-methyl-6H-thieno[2,3-b]pyrrol-4-yl)acetate [prepared using B from the methyl 2-(5-methyl-6H-thieno[2,3-b]pyrrol-4-yl)acetate and the 4-(bromomethyl)-N,N-dimethylbenzenesulfonamide [AmberMolTech LLC]] | 2-(6-(4-(N,N-Dimethylsulfamoyl)benzyl)-5-methyl-6H-thieno[2,3-b]pyrrol-4-yl)acetic acid | D.1.6 | 2.46 (b) | 393.1 (M + H)$^+$ |
| Methyl 2-(6-(4-(N-cyclohexyl-N-methylsulfamoyl)benzyl)-5-methyl-6H-thieno[2,3-b]pyrrol-4-yl)acetate [prepared using B from the methyl 2-(5-methyl-6H-thieno[2,3-b]pyrrol-4-yl)acetate and the 4-(bromomethyl)-N-cyclohexyl-N-methylbenzene-sulfonamide[prepared using J with the The 4-(bromo-methyl)benzene-1-sulfonyl chloride and the N-methylcyclohexanamine]] | 2-(6-(4-(N-Cyclohexyl-N-methylsulfamoyl)benzyl)-5-methyl-6H-thieno[2,3-b]pyrrol-4-yl)acetic acid | D.1.5 | 2.95 (b) | 461.2 (M + H)$^+$ |
| Methyl 2-(5-methyl-6-(4-(morpholinosulfonyl)benzyl)-6H-thieno[2,3-b]pyrrol-4-yl)acetate [prepared using B from the methyl 2-(5-methyl-6H-thieno[2,3-b]pyrrol-4-yl)acetate and the 4-(4-(bromomethyl)phenylsulfonyl)morpholine [prepared using J from the 4-(bromomethyl)benzene-1-sulfonyl chloride and morpholine]] | 2-(5-Methyl-6-(4-(morpholinosulfonyl)benzyl)-6H-thieno[2,3-b]pyrrol-4-yl)acetic acid | D.1.7 | 2.43 (b) | 435.1 (M + H)$^+$ |
| Methyl 2-(5-methyl-6-((5-methylisoxazol-3-yl)methyl)-6H-thieno[2,3-b]pyrrol-4-yl)acetate [prepared using B from the methyl 2-(5-methyl-6H-thieno[2,3-b]pyrrol-4-yl)acetate and the 3-(bromomethyl)-5-methylisoxazole [Ryan Scientific Product List] | 2-(5-Methyl-6-((5-methylisoxazol-3-yl)methyl)-6H-thieno[2,3-b]pyrrol-4-yl)acetic acid | D.1.8 | 2.35 (a) | 291.08 (M + H)$^+$ |

TABLE D.2

Examples of 2-(6-benzyl-2,5-dimethyl-6H-thieno[2,3-b]pyrrol-4-yl)acetic acidusing General Procedure D

| Ester | Product | Example # | R_t min (method) | m/z ESI |
|---|---|---|---|---|
| Methyl 2-(2,5-dimethyl-6-(4-(methylsulfonyl)benzyl)-6H-thieno[2,3-b]pyrrol-4-yl)acetate [prepared using A. from the methyl 2-(2,5-dimethyl-6H-thieno[2,3-b]pyrrol-4-yl)acetate and the 1-(chloromethyl)-4-(methylsulfonyl)benzene [Oakwood Products Inc]] | 2-(2,5-Dimethyl-6-(4-(methylsulfonyl)benzyl)-6H-thieno[2,3-b]pyrrol-4-yl)acetic acid | D.2.1 | 2.38 (a) | 376 (M − H)$^-$ |
| Methyl 2-(6-(2-chloro-4-(methylsulfonyl)benzyl)-2,5-dimethyl-6H-thieno[2,3-b]pyrrol- | 2-(6-(2-Chloro-4-(methylsulfonyl)benzyl)-2,5-dimethyl-6H- | D.2.2 | 2.50 (a) | 410 (M − H)$^-$ |

TABLE D.2-continued

Examples of 2-(6-benzyl-2,5-dimethyl-6H-thieno[2,3-b]pyrrol-4-yl)acetic acid using General Procedure D

| Ester | Product | Example # | R$_t$ min (method) | m/z ESI |
|---|---|---|---|---|
| 4-yl)acetate [prepared using A from the methyl 2-(2,5-dimethyl-6H-thieno[2,3-b]pyrrol-4-yl)acetate and the 2-chloro-1-(bromomethyl)-4-(methylsulfonyl)benzene [Oakwood Products Inc]] | thieno[2,3-b]pyrrol-4-yl)acetic acid | | | |

TABLE D.3

Examples of 2-(6-benzyl-3,5-dimethyl-6H-thieno[2,3-b]pyrrol-4-yl)acetic acid acid using General Procedure D

| Ester | Product | Example # | R$_t$ min (method) | m/z ESI |
|---|---|---|---|---|
| Methyl 2-(3,5-dimethyl-6-(4-(methylsulfonyl)benzyl)-6H-thieno[2,3-b]pyrrol-4-yl)acetate [prepared using A from the methyl 2-(3,5-dimethyl-6H-thieno[2,3-b]pyrrol-4-yl)acetate and the 1-(chloromethyl)-4-(methylsulfonyl)benzene [Oakwood Products Inc]] | 2-(3,5-Dimethyl-6-(4-(methylsulfonyl)benzyl)-6H-thieno[2,3-b]pyrrol-4-yl)acetic acid | D.3.1 | 1.96 (a) | 376 (M − H)$^−$ |

General Procedure E: Saponification of a thiophene-2-carboxylate

To a solution of an appropriately substituted thiophene-2-carboxylate in an organic solvent (such as dioxane or THF preferably THF) is added an aqueous solution of a base (such as NaOH, KOH or LiOH, preferably NaOH) (0.9-2.0 equiv, preferably 1.1 equiv). A protic solvent (such as MeOH or EtOH, preferably MeOH) is added to the reaction mixture until an homogeneous solution is obtained. After about 2-8 h (preferably 4 h), an acid (such AcOH or HCl, as preferably HCl) is added until a pH of about 1 is obtained. The reaction mixture is partially concentrated and the resulting solid is collected by filtration and dried in vacuo.

Illustration of General Procedure E:

Preparation #E.1: The 3-iodo-4-methylthiophene-2-carboxylic acid

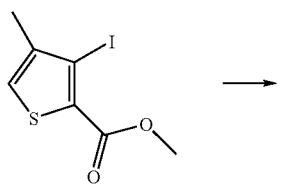

To a solution of methyl 3-iodo-4-methylthiophene-2-carboxylate [Oakwood Product Inc.] (10 g, 35.4 mmol) in THF (200 mL) was added a solution of 2N NaOH (19.50 mL, 39.0 mmol). MeOH was added to the reaction mixture until a homogeneous solution was obtained. After about 4 h, concentrated HCl was added until a pH of about 1 was obtained. The reaction mixture was partially concentrated under reduced pressure and the resulting solid was collected by filtration and dried under reduced pressure to provide the title compound as a brown solid (9.50 g, 100%): LC/MS (Table 1, Method a) R$_t$=2.55 min; m/z: 267 (M–H)$^−$.

General Procedure F: Formation of a tert-butyl thiophen-2-ylcarbamate

To a solution of an appropriately substituted thiophene-2-carboxylic acid (preferably 1 equiv) in tert-butanol is added an amine (Et$_3$N, N,N-diisopropylamine, N,N-diisopropylethylamine, preferably Et$_3$N) (1-3 equiv, preferably 1 equiv) and diphenyl phosphoryl azide (1-3 equiv, preferably 1 equiv) at about 15-25° C. (preferably at about 20° C.). The reaction mixture is heated to about 25° C. to 65° C. to reflux (preferably to about 65° C.) for about 2-16 h (preferably about 8 h). The volatiles are removed under reduced pressure and the residue optionally purified by chromatography on silica gel.

Illustration of General Procedure F

Preparation #F.1: The tert-butyl 5-methylthiophen-2-ylcarbamate

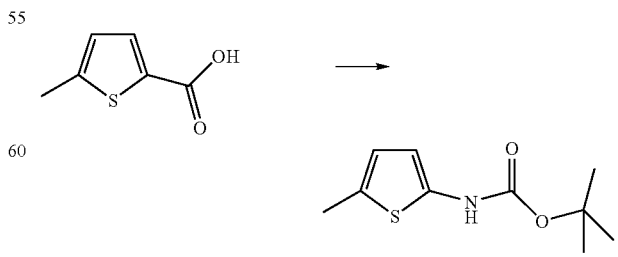

To a solution of 5-methylthiophene-2-carboxylic acid (5 g, 35.2 mmol) in tert-butanol (99 mL) was added Et$_3$N (3.91 g, 38.7 mmol) and diphenyl phosphoryl azide (10.65 g, 38.7 mmol). The reaction mixture was heated to 65° C. for 4 h, then refluxed for 4 h. The volatiles were removed under reduced pressure and the residual crude material was purified by flash chromatography on silica gel (DCM/MeOH: 98/2) to give the title compound (7 g, 75%): $^1$HNMR (DMSO) δ 10.10 (s, 1H), 6.43 (d, J=2 Hz, 1H), 6.29 (d, J=2 Hz, 1H), 2.30 (s, 3H), 1.42 (s, 9H).

General Procedure G: Bromination of a tert-butyl thiophen-2-ylcarbamate

To a solution of a tert-butyl thiophen-2-ylcarbamate (preferably 1 equiv) in an alcoholic solvent (MeOH, EtOH, i-PrOH, preferably MeOH) at about −5 to 5° C. (preferably at about 0° C.) is added a solution of bromine (1-2 equiv, preferably 1 equiv) in an alcoholic solvent (MeOH, EtOH, i-PrOH, preferably MeOH) during about 1-2 h (preferably about 1 h). The reaction is stirred at about −5 to 5° C. (preferably at about 0° C.) for about 15 min to 2 h (preferably about 1 h) and at about 10 to 25° C. (preferably about 20° C.) for about 0.5 to 2 h (preferably about 1 h). The reaction is then poured into water and the solution is neutralized with an aqueous solution of a base (such as NaOH, KOH, NaHCO$_3$, Na$_2$CO$_3$, preferably NaOH). MeOH is removed under reduced pressure and the product is extracted into an organic solvent (DCM, EtOAc, Et$_2$O, preferably DCM). The combined organic phases are dried over a drying agent (such as MgSO$_4$, NaSO$_4$, preferably MgSO$_4$). The solvent is removed under reduced pressure to give the title compound that can optionally be purified by chromatography on silica gel.

Illustration of General Procedure G

Preparation #G.1: The tert-butyl 3-bromo-5-methylthiophen-2-ylcarbamate

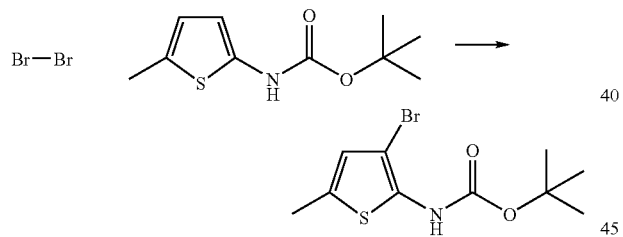

To a solution of tert-butyl 5-methylthiophen-2-ylcarbamate (5.1 g, 23.91 mmol) in MeOH (478 mL) at 0° C. was added drop wise a solution of bromine (1.232 mL, 23.91 mmol) in MeOH (478 mL) during 1.5 h. The reaction mixture was then stirred at 0° C. for 0.5 h and at ambient temperature for 45 min. The reaction was poured into water (400 mL) and the solution was neutralized with 2 M NaOH (aq). MeOH was removed under reduced pressure and the cloudy aqueous phase was extracted with DCM (3×200 mL). The combined organic phases were dried over MgSO$_4$. The solvent was removed under reduced pressure to give (5.3 g, 76%) of the title compound that was used in the next step without further purification: LC/MS (Table 1, Method a) R$_t$=2.48 min; m/z: 292.1 (M−H)$^-$.

General Procedure H: One pot alkylation/cyclization to a tert-butyl 6H-thieno[2,3-b]pyrrole-6-carboxylates To a solution of a tert-butyl 3-bromo- or tert-butyl 3-iodothiophen-2-ylcarbamate (preferably 1 equiv) in an organic solvent (such as DMF, DMA or dioxane, preferably DMF) at ambient temperature is added a carbonate (such as K$_2$CO$_3$, or Na$_2$CO$_3$, preferably K$_2$CO$_3$) (1-5 equiv, preferably 4 equiv) and an (E)-4-bromoalkyl-2-enoate (1-2 equiv, preferably 2 equiv). The reaction mixture is stirred at ambient temperature for about 12-18 h (preferably 18 h). Palladium (II) acetate (0.05-0.10 equiv, preferably 0.05 equiv) and PPh$_3$ (0.05-0.15 equiv, preferably 0.1 equiv) are added and the reaction mixture is heated to about 75-100° C. (preferably 85° C.) for about 4-18 h (preferably 16 h). The crude mixture is diluted with an organic solvent (such as EtOAc, DCM, or Et$_2$O, preferably DCM) and washed with water. The layers are separated and the organic solution is dried over a drying agent (such as Na$_2$SO$_4$ or MgSO$_4$, preferably MgSO$_4$), filtered, and concentrated under reduced pressure to give the target compound. Optionally, the product can be purified by chromatography on silica gel.

Illustration of General Procedure H

Preparation #H.1: the tert-Butyl 4-(2-methoxy-2-oxoethyl)-5-methyl-6H-thieno[2,3-b]pyrrole-6-carboxylate

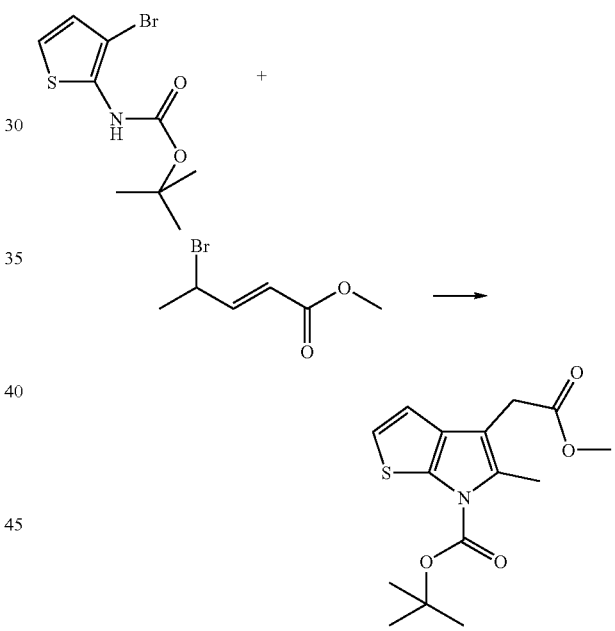

To a solution of tert-butyl 3-bromothiophen-2-ylcarbamate (1 g, 3.59 mmol) in DMF (15 mL) was added K$_2$CO$_3$ (1.987 g, 14.38 mmol) and (E)-methyl 4-bromopent-2-enoate (prepared according to C. Girard et al, *TL*, vol 30, No. 52, pp 7399-7402, 1989) (1.388 g, 7.19 mmol). The reaction mixture was stirred at ambient temperature for 16 h. Palladium(II) acetate (0.040 g, 0.180 mmol) and PPh$_3$ (0.094 g, 0.359 mmol) were added and the reaction mixture was heated to 85° C. for 18 h. DCM was added and the resulting solution was washed with water. The layers were separated and the organic solution was dried over MgSO$_4$, filtered, and concentrated under reduced pressure. The crude material was purified by flash chromatography on silica gel (heptane/EtOAc: 95/5 to 55/45) to give the title compound (0.404 g, 36.3%): LC/MS (Table 1, Method d) R$_t$=2.40 min; MS m/z 310 (M+H)$^+$; $^1$H NMR (CDCl$_3$) δ 6.97 (m, 2H), 3.72 (s, 3H), 3.62 (s, 2H), 2.56 (s, 3H), 1.70 (s, 9H).

General Procedure I: Deprotection of a tert-butyl 6H-thieno[2,3-b]pyrrole-6-carboxylate To a solution of a tert-butyl 4-(2-alkoxy-2-oxoethyl)-6H-thieno[2,3-b]pyrrole-6-carboxylate (preferably 1 equiv) in an organic solvent (such as DCM, EtOAc, Et₂O, preferably DCM) is added silica gel. The volatiles are evaporated under reduced pressure and the residue is heated to about 30 to 100° C. (preferably to about 65° C.) under vacuum for about 8 to 48 h (preferably about 24 h). The compound is washed off the silica gel by an organic solvent (such as DCM, EtOAc, Et₂O, preferably DCM). The residue can optionally be purified by chromatography on silica gel.

Illustration of General Procedure I

Preparation #E.1: The methyl 2-(2,5-dimethyl-6H-thieno[2,3-b]pyrrol-4-yl)acetate

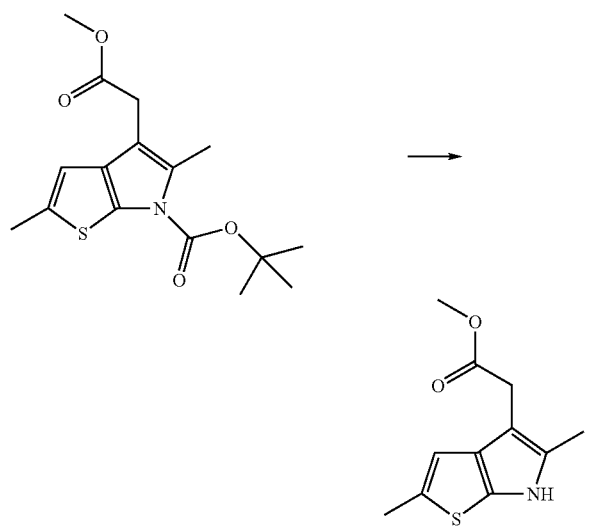

To a solution of tert-butyl 4-(2-methoxy-2-oxoethyl)-2,5-dimethyl-6H-thieno[2,3-b]pyrrole-6-carboxylate (0.790 g, 2.443 mmol) in DCM (13.13 mL) was added 13 mL of silica gel. The mixture was concentrated under reduced pressure and the residue was heated to 65° C. under vacuum for 24 h. The reaction mixture was purified by flash chromatography on silica gel (EtOAc/heptane 15/85), to give the title compound (0.35 g, 64%): LC/MS (Table 1, Method a) R$_t$=2.06 min; MS m/z 222.1 (M−H)⁻.

General Procedure J: Preparation of 4-(halomethyl)benzenesulfonamides

A 4-(halomethyl)benzene-1-sulfonyl chloride (such as the 4-(bromomethyl)benzene-1-sulfonyl chloride or 4-(chloromethyl)benzene-1-sulfonyl chloride, preferably 4-(bromomethyl)benzene-1-sulfonyl chloride) (preferably 1 equiv) is reacted with a primary or secondary amine (1-1.5 equiv, preferably 1.5 equiv) in the presence of a base (such as Et₃N, or N-methyldiisopropylamine, preferably Et₃N) (1-2 equiv, preferably 1.5 equiv) in an organic solvent (such as THF or DCM, preferably THF) at about ambient temperature for about 5-24 h (preferably 24 h). The crude reaction mixture is diluted with DCM and washed with water. The organics extracts are dried over a drying agent (such as Na₂SO₄ or MgSO₄, preferably MgSO₄), filtered, concentrated under reduced pressure and the resulting crude material optionally purified by chromatography on silica gel.

Illustration of General Procedure J: The 4-(bromomethyl)-N-cyclohexyl-N-methylbenzenesulfonamide

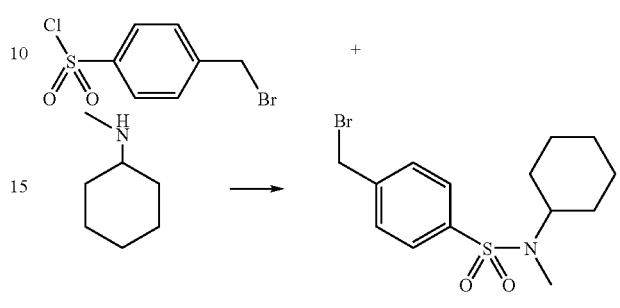

The 4-(bromomethyl)benzene-1-sulfonyl chloride (1 g, 3.71 mmol), Et₃N (0.776 mL, 5.56 mmol) and N-methylcyclohexylamine (0.42 g, 3.71 mmol) were reacted overnight in THF (6 mL) at ambient temperature. The mixture was diluted with DCM and washed with water. The organics were dried over MgSO₄, filtered, concentrated and purified by chromatography on silica gel using an heptane/EtOAc gradient (100/0 to 50/50) to give the title compound (0.317 g, 24.6%): ¹H NMR (CDCl₃) δ 7.88-7.77 (d, 2H, J=8.4 Hz), 7.52 (d, 2H, J=8.4 Hz), 4.62 (s, 2H), 3.87-3.60 (m, 1H), 2.75 (s, 3H), 1.79-1.69 (m, 2H), 1.66-1.57 (m, 1H), 1.52-1.50 (m, 1H), 1.30 (m, 4H), 1.14-0.84 (m, 2H)

General Procedure K: Coupling of a 4H-thieno[3,2-b]pyrrole with sulfonylchlorides A solution of alkoxide (tBuOK, tBuONa, NaOEt, NaOMe, preferably tBuOK) (1-1.5 equiv, preferably 1.2 equiv) is added to a solution of an alkyl 2-(4H-thieno[3,2-b]pyrrol-6-yl)acetate (1.0 equiv.) in an organic solvent (such as THF or dioxane, preferably THF). The reaction mixture is stirred or shaken at about ambient temperature for about 10 min-2 h (preferably, 10 min). A sulfonyl chloride (1-1.5 equiv, preferably 1.2 equiv) in solution in an organic solvent (such as THF or dioxane, preferably THF) is added and the mixture stirred or shaken at about ambient temperature for about 2-6 h (preferably 4 h). An aqueous solution of a base (such as NaOH, KOH or LiOH preferably NaOH) (1-10 equiv, preferably 9.5 equiv) is added and the mixture reacted at about ambient temperature for about 12-24 h (preferably 24 h). The crude mixture is concentrated under vacuum purified by HPLC.

Illustration of General Procedure K

Example K.1.1: 2-(4-(Cyclopropylsulfonyl)-4H-thieno[3,2-b]pyrrol-6-yl)acetic acid

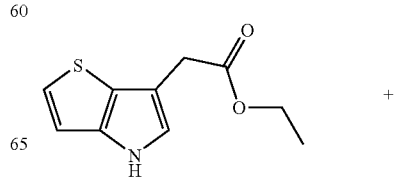

-continued

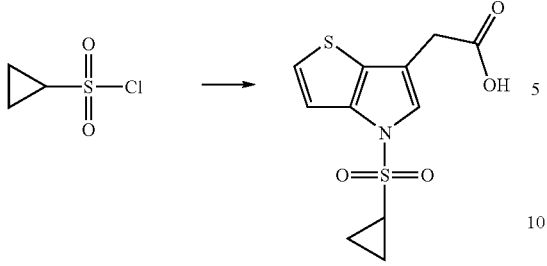

A solution of tBuOK (0.1 mL, 1.2 equiv, 1.0 M in THF) was added to a solution of ethyl 2-(4H-thieno[3,2-b]pyrrol-6-yl) acetate (0.024 g, 0.11 mmol, 1.0 equiv.) in THF (0.5 mL) in a 20 mL vial. This vial was capped and shaken at room temperature for 10 min. To the mixture a solution of cyclopropanesulfonyl chloride (0.7 mL, 1.2 equiv, 0.2 M in THF) was added and the reaction was shaken at room temperature for 4 h. After which time NaOH (aqueous) (1.0 mL, 1.0 M, 9.5 equiv) was added and the reaction was shaken at room temperature overnight. The crude reaction mixture was then concentrated to dryness under reduced pressure and taken up in 1.5 mL 1:1 DMSO/MeOH and purified by reverse phase HPLC (Table 1, Method h) to give the title compound (0.001 g, 3.11%): LC/MS (Table 1, Method e) $R_t$=1.29 min; MS m/z 285.9 (M+H)$^+$.

TABLE K.1

Examples of 2-(4-(sulfonyl)-4H-thieno[3,2-b]pyrrol-6-yl)acetic acids prepared from the ethyl 2-(4H-thieno[3,2-b]pyrrol-6-yl)acetate using General Procedure K

| Sulfonyl chloride | Product | Example # | $R_t$ min (method) | m/z ESI |
|---|---|---|---|---|
| 2,4,6-Trimethylbenzene-1-sulfonyl chloride | 2-(4-(Mesitylsulfonyl)-4H-thieno[3,2-b]pyrrol-6-yl)acetic acid | K.1.2 | 1.69 (e) | 364 (M + H)$^+$ |
| 2,2,4,6,7-Pentamethyl-2,3-dihydrobenzofuran-5-sulfonyl chloride | 2-(4-(2,2,4,6,7-Pentamethyl-2,3-dihydrobenzofuran-5-ylsulfonyl)-4H-thieno[3,2-b]pyrrol-6-yl)acetic acid | K.1.3 | 1.84 (e) | 434 (M + H)$^+$ |
| 4-Methoxy-2,3,6-trimethylbenzene-1-sulfonyl chloride | 2-(4-(4-Methoxy-2,3,6-trimethylphenylsulfonyl)-4H-thieno[3,2-b]pyrrol-6-yl)acetic acid | K.1.4 | 1.72 (e) | 394 (M + H)$^+$ |
| 4-Methylsulfonylbenzenesulfonyl chloride | 2-(4-(4-(Methylsulfonyl)phenylsulfonyl)-4H-thieno[3,2-b]pyrrol-6-yl)acetic acid | K.1.5 | 1.87 (a) | 398.0 (M − H)$^-$ |
| 4-Chlorobenzenesulfonyl chloride | 2-(4-(4-Chlorophenylsulfonyl)-4H-thieno[3,2-b]pyrrol-6-yl)acetic acid | K.1.6 | 2.42 (a) | 354.0 (M − H)$^-$ |
| 2,5-Dichlorobenzenesulfonyl chloride | 2-(4-(2,5-Dichlorophenylsulfonyl)-4H-thieno[3,2-b]pyrrol-6-yl)acetic acid | K.1.7 | 2.42 (a) | 388.0 (M − H)$^-$ |
| 2-Naphthalenesulfonyl chloride | 2-(4-(Naphthalen-1-ylsulfonyl)-4H-thieno[3,2-b]pyrrol-6-yl)acetic acid | K.1.8 | 2.49 (a) | 370.1 (M − H)$^-$ |
| 5-Bromo-2-methoxybenzene-1-sulfonyl chloride | 2-(4-(5-Bromo-2-methoxyphenylsulfonyl)-4H-thieno[3,2-b]pyrrol-6-yl)acetic acid | K.1.10 | 1.63 (e) | 429.0 (M − H)$^-$ |
| 3-Cyano-4-fluorobenzene-1-sulfonyl chloride | 2-(4-(3-Cyano-4-hydroxyphenylsulfonyl)-4H-thieno[3,2-b]pyrrol-6-yl)acetic acid | K.1.11 | 1.39 (e) | 361.0 (M − H)$^-$ |
| 2-Bromo-4,6-difluorobenzene-1-sulfonyl chloride | 2-(4-(2-Bromo-6-fluoro-4-hydroxyphenylsulfonyl)-4H-thieno[3,2-b]pyrrol-6-yl)acetic acid | K.1.12 | 1.49 (e) | 433.0 (M − H)$^-$ |
| 2-Bromo-4-fluorobenzene-1-sulfonyl chloride | 2-(4-(2-Bromo-4-hydroxyphenylsulfonyl)-4H-thieno[3,2-b]pyrrol-6-yl)acetic acid | K.1.13 | 1.45 (e) | 415.0 (M − H)$^-$ |
| 4-Methoxy-2-methylbenzene-1-sulfonyl chloride | 2-(4-(4-Methoxy-2-methylphenylsulfonyl)-4H-thieno[3,2-b]pyrrol-6-yl)acetic acid | K.1.14 | 1.56 (e) | 364.0 (M − H)$^-$ |

What is claimed:

1. A compound of Formula I

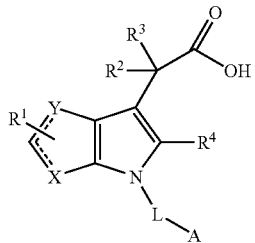

Formula I pharmaceutically acceptable salts, enantiomers or stereoisomers thereof, wherein
X is CH, S or N;
Y is CH, S or N;
L is SO, S(O)$_2$ or (C$_1$-C$_4$)alkyl;
A is optionally substituted aryl, optionally substituted (C$_3$-C$_6$)cycloalkyl, optionally substituted heteroaryl, optionally substituted heterocyclyl or optionally substituted aryl-S(O)$_2$ —Z;
wherein Z is N(R$^5$)$_2$, optionally substituted (C$_1$-C$_6$) alkyl, optionally substituted (C$_3$-C$_6$)cycloalkyl or optionally substituted heterocyclyl;
R$^1$, R$^2$, R$^3$ and R$^4$ are independently H or (C$_1$-C$_4$)alkyl; and
R$^5$ is independently H, (C$_1$-C$_3$)alkyl, (C$_3$-C$_6$)cycloalkyl, —CO—(C$_1$-C$_6$)alkyl, or —CON(R$^1$)$_2$;
provided that X and Y are not both S, not both CH$_2$ and not both N.

2. The compound of claim 1 wherein X is CH.
3. The compound of claim 2 wherein Y is S.
4. The compound of claim 3 wherein L is S(O)$_2$.
5. The compound of claim 4 wherein A is optionally substituted phenyl, optionally substituted naphthyl, optionally substituted (C$_3$-C$_6$)cycloalkyl or optionally substituted dihydrobenzofuranyl; and
R$^1$, R$^2$, R$^3$ and R$^4$ are independently H.
6. The compound of claim 5 wherein
A is optionally substituted phenyl, optionally substituted dihydrobenzofuranyl or optionally substituted cyclopropyl;
wherein the phenyl, the dihydrobenzofuranyl or the cyclopropyl is optionally substituted with one or more substituents independently selected from halogen, CN, OH, —SO$_2$—(C$_1$-C$_6$)alkyl, —SO$_2$—(C$_3$-C$_6$)cycloalkyl, —O—(C$_1$-C$_4$)alkyl and optionally substituted (C$_1$-C$_6$) alkyl.
7. The compound of claim 1 wherein X is S.
8. The compound of claim 7 wherein Y is CH.
9. The compound of claim 8 wherein L is S(O)$_2$ or (C$_1$-C$_4$) alkyl.
10. The compound of claim 9 wherein A is optionally substituted aryl, optionally substituted heteroaryl or optionally substituted -aryl-S(O)$_2$—Z;
wherein Z is N(R$^5$)$_2$, optionally substituted (C$_1$-C$_6$)alkyl, optionally substituted (C$_3$-C$_6$)cycloalkyl or optionally substituted heterocyclyl; and
R$^5$ is independently H, (C$_1$-C$_3$)alkyl, or (C$_3$-C$_6$)cycloalkyl, —CO—(C$_1$-C$_6$)alkyl, or —CON(R$^1$)$_2$.
11. The compound of claim 10 wherein R$^2$ and R$^3$ are H.
12. The compound of claim 11 wherein A is optionally substituted isoxazolyl, optionally substituted naphthyl, optionally substituted phenyl, optionally substituted pyridinyl or optionally substituted phenyl-S(O)$_2$—Z;
wherein Z is CH$_3$, —N(CH$_3$)$_2$, —N(CH$_3$)cyclohexyl, optionally substituted morpholinyl or optionally substituted pyrrolidinyl.
13. The compound of claim 12 wherein A is optionally substituted by one or more substituents independently selected from halogen, CN, CH$_3$, —NH—C(O)—CH$_3$, NHCON(CH$_3$)$_2$, CF$_3$, —S(O)$_2$CH$_3$, optionally substituted (C$_1$-C$_4$)alkyl, —O—(C$_1$-C$_4$)alkyl and pyrazolyl.
14. The compound of claim 13 wherein R$^1$ is CH$_3$ and R$^4$ is CH$_3$.
15. The compound of claim 13 wherein R$^1$ is H and R$^4$ is H or CH$_3$.
16. The compound of claim 15 wherein L is CH$_2$.
17. The compound of claim 16 wherein A is optionally substituted isoxazolyl, optionally substituted phenyl or optionally substituted -phenyl-S(O)$_2$—Z;
wherein Z is CH$_3$, —N(CH$_3$)$_2$, —N(CH$_3$)cyclohexyl or optionally substituted morpholinyl.
18. The compound of claim 15 wherein L is S(O)$_2$.
19. The compound of claim 18 wherein A is optionally substituted naphthyl, optionally substituted phenyl, optionally substituted pyridinyl or optionally substituted -phenyl-S(O)$_2$—Z;
wherein Z is CH$_3$, —N(CH$_3$)$_2$, optionally substituted morpholinyl or optionally substituted pyrrolidinyl.
20. A method of treating a condition in a patient comprising administering a therapeutically effective amount of a compound of Formula I

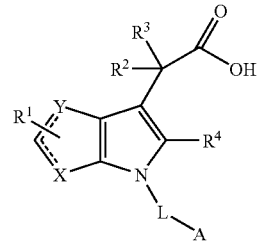

Formula I pharmaceutically acceptable salts, enantiomers or stereoisomers thereof, wherein
X is CH, S or N;
Y is CH, S or N;
L is SO, S(O)$_2$ or (C$_1$-C$_4$)alkyl;
A is optionally substituted aryl, optionally substituted (C$_3$-C$_6$)cycloalkyl, optionally substituted heteroaryl, optionally substituted heterocyclyl or optionally substituted -aryl-S(O)$_2$—Z;
wherein Z is N(R$^5$)$_2$, optionally substituted (C$_1$-C$_6$) alkyl, optionally substituted (C$_3$-C$_6$)cycloalkyl or optionally substituted heterocyclyl;
R$^1$, R$^2$, R$^3$ and R$^4$ are independently H or (C$_1$-C$_4$)alkyl; and
R$^5$ is independently H, (C$_1$-C$_3$)alkyl, (C$_3$-C$_6$)cycloalkyl, —CO—(C$_1$-C$_6$)alkyl, or —CON(R$^1$)$_2$;
provided that X and Y are not both S, not both CH$_2$ and not both N;
to said patient in need thereof, wherein the condition is asthma, allergic asthma, allergic inflammation, rhinitis, allergic rhinitis or atopic dermatitis.

* * * * *